(12) United States Patent
Wieczorek et al.

(10) Patent No.: US 11,925,607 B2
(45) Date of Patent: Mar. 12, 2024

(54) KETAMINE COMPOSITION FOR USE IN A METHOD OF TREATMENT OF DEPRESSION BY PULMONARY ADMINISTRATION

(71) Applicant: Celon Pharma S.A., Kielpin/Lomianki (PL)

(72) Inventors: Maciej Wieczorek, Kielpin/Lomianki (PL); Sylwia Janowska, Kielpin/Lomianki (PL)

(73) Assignee: CELON PHARMA S.A., Kielpin/Lomianki (PL)

( * ) Notice: Subject to any disclaimer, the term of this patent is extended or adjusted under 35 U.S.C. 154(b) by 0 days.

(21) Appl. No.: 17/281,136

(22) PCT Filed: Sep. 24, 2019

(86) PCT No.: PCT/EP2019/075735
§ 371 (c)(1),
(2) Date: Mar. 29, 2021

(87) PCT Pub. No.: WO2020/064748
PCT Pub. Date: Apr. 2, 2020

(65) Prior Publication Data
US 2021/0353560 A1   Nov. 18, 2021

(30) Foreign Application Priority Data
Sep. 28, 2018  (EP) .................... 18461615

(51) Int. Cl.
*A61K 31/135* (2006.01)
*A61K 9/00* (2006.01)
*A61P 25/24* (2006.01)

(52) U.S. Cl.
CPC .......... *A61K 31/135* (2013.01); *A61K 9/0075* (2013.01)

(58) Field of Classification Search
CPC ...... A61K 31/135; A61K 9/0075; A61P 25/24
See application file for complete search history.

(56) References Cited

U.S. PATENT DOCUMENTS

| | | | | |
|---|---|---|---|---|
| 2008/0132531 A1* | 6/2008 | Holtman | .................. | A61P 25/04 514/183 |
| 2015/0050350 A1* | 2/2015 | Staniforth | .............. | A61K 31/58 424/490 |
| 2015/0328159 A1* | 11/2015 | Whitfield | ............. | A61K 9/1694 424/85.4 |
| 2017/0151191 A1* | 6/2017 | Charney | ............... | A61M 15/08 |
| 2020/0337999 A1* | 10/2020 | Wieczorek | .............. | A61P 25/24 |

FOREIGN PATENT DOCUMENTS

WO  WO 2019/129397 A1  7/2019

OTHER PUBLICATIONS

International Search Report dated Dec. 17, 2019 in connection with PCT International Application No. PCT/EP2019/075735.
Written Opinion (form PCT/ISA/237) dated Dec. 17, 2019 in connection with PCT International Application No. PCT/EP2019/075735.
International Preliminary Report on Patentability dated Mar. 23, 2021 in connection with PCT International Application No. PCT/EP2019/075735.
Anonymous: "Safety and Pharmacokinetic Study of Inhaled Esketamine in Healthy Volunteers." ClinicalTrials.gov, Jul. 12, 2018, pp. 1-8.
Canuso, C. M. et al. "Efficacy and Safety of Intranasal Esketamine for the Rapid Reduction of Symptoms of Depression and Suicidality lin Patients at Imminent Risk for Suicide: Results of a Double-Blind, Randomized, Placebo-Controlled Study." American Journal of Psychiatry., vol. 175, No. 7, Apr. 11, 2018, pp. 620-630.
Jonkman, K. et al. "Ketamine inhalation." British Journal of Anaesthesia., vol. 118, No. 2, Feb. 2017, pp. 268-269.
Jonkman, K. et al. "Pharmacokinetics and Bioavailability of Inhaled Esketamine in Healthy Volunteers." Anesthesiology., vol. 127, No. 4, Oct. 2017, pp. 675-683.

* cited by examiner

*Primary Examiner* — Mina Haghighatian
(74) *Attorney, Agent, or Firm* — Gary J. Gershik

(57) ABSTRACT

An inhalable pharmaceutical composition comprising ketamine or its pharmaceutically acceptable salt for use in a method of treatment of depression by administration via pulmonary route, treatment comprising cycle of multiple sequences of administration by inhalation, said cycle lasting from 10 days to 30 days, wherein each of multiple sequences of administration is performed in a one single day, with 2 to 4 days intervals between sequences, and each of said sequences consists of multiple single dose inhalations separated by a break period lasting at least 5 minutes. The composition is especially useful for the treatment of treatment-resistant depression.

20 Claims, 16 Drawing Sheets

KETAMINE COMPOSITION FOR USE IN A METHOD OF TREATMENT OF DEPRESSION BY PULMONARY ADMINISTRATION

RELATED APPLICATIONS

This application is a § 371 national stage of PCT International Application No. PCT/EP2019/075735, filed Sep. 24, 2019, claiming priority of European Patent Application No. 18461615.9, filed Sep. 28, 2018, the contents of each of which are hereby incorporated by reference into this application.

TECHNICAL FIELD

The present invention relates to an inhalable pharmaceutical composition comprising ketamine, in particular inhalable dry powder formulation for use in a method of treatment of depression, including major depressive disorder, bipolar disorder and treatment-resistant depression. In particular, the invention relates to a dosage regimen of said inhalable pharmaceutical composition in treatment of depression.

BACKGROUND ART

Depression, especially major depressive disorder, bipolar disorder and treatment-resistant depression, is a serious problem in a modern society. Many treatment options have been developed for treating depression, including monotherapy or combination therapy in a convenient for patients oral administration regimen. However, there is a relatively high percentage of patients that are treatment-refractory or partially or totally treatment-resistant to existing antidepressants. In practice, at present the only real choice in such severe cases can be electroshocks.

Ketamine is a known anesthetic and analgesic, used for anesthesia and in the treatment of chronic pain. Ketamine is a chiral compound and can exist as a racemate and as S-enantiomer (known as esketamine) or R-enantiomer (known as arketamine). Ketamine can form a pharmaceutically acceptable salts and in pharmaceutical applications is generally used as preferred hydrochloride salt. The optical rotation of an enantiomer varies between ketamine and its salts. For example, while esketamine free base is dextrarotatory S-(+), esketamine hydrochloride is levorotatory S-(−).

Since about one decade antidepressant activity of ketamine and its S-isomer (esketamine) is explored, especially in the treatment of treatment-resistant or treatment refractory depression (G. Serafini et al., The Role of Ketamine in Treatment-Resistant Depression: A Systematic Review, Current Neuropharmacology, 2014, 12, 444-461). Treatment-resistant depression is a term used in clinical psychiatry to describe cases of major depressive disorder that do not respond adequately to appropriate courses of at least two antidepressants in a suitable dose for a suitable time.

Data collected up to now show exceptional properties of ketamine and esketamine. The effect is very quick (after 2-3 hours from administration) and relatively long-lasting—a few days after single dose of a medicament. The rapidity of the clinical effect is surprisingly high and unexpected, since the effect of antidepressants present on the market appears after at least two weeks, even three to four weeks of day-to-day administration. Therefore, ketamine or esketamine could be used as a drug of first choice in patients with major depression with enhanced suicide risk that are resistant to existing oral antidepressants. The scale of the effect is also very high; about ⅔ of the patients with treatment-resistant depression is responsive to ketamine treatment.

The knowledge of the pharmacology of ketamine is still poor. As a dissociative anesthetic, the drug may exert dissociative and psychomimetic effects (DP). Available data show that this effects are correlated with systemic concentration of the drug. Dissociative and psychomimetic effects are among most often observed side-effects and significantly lower the comfort of patients. However, there are still groups of patients that respond to the treatment with ketamine without experiencing DP effects. Hence, still exists a therapeutic window, although narrow, for effective and safe use of ketamine in the treatment of depression without DP.

Ketamine undergoes extensive first-pass metabolism effect in the liver. Primarily, norketamine is produced as the initial metabolite. Norketamine is then metabolized to further metabolites. The knowledge about norketamine and further metabolites is still not full. On the level of action on NMDA receptor norketamine is many times less active than ketamine. Other metabolites are also mostly less active than ketamine. Furthermore, little is known about toxicity of norketamine and other metabolites. This, in combination with high individual variations of their concentrations dependent on the status of hepatic enzymes, as a rule makes them undesired compounds. There are also reports on correlation of some hydroxylated metabolites of ketamine with psychotic and dissociative symptoms.

In previous studies ketamine and esketamine were administered in the treatment of depression intravenously or intranasally. Attempts of oral administration were generally unsuccessful or the effects were observed only after several weeks of administration.

Literature describes many examples of ketamine pharmacokinetics depending on the administration route.

Administration route with currently expected minimum level of metabolites is an intravenous one. After intravenous infusion of racemic ketamine at 0.5 mg/kg for 40 minutes, the parent drug maintains its systemic concentration about 200 ng/ml for about 40 minutes, afterwards the concentration falls down quickly with a half-period below 2 hours. Simultaneously, norketamine reaches its maximum concentration at the level of 10-20% of ketamine concentration. The percentage of area-under-curve (AUC) norketamine to ketamine is about 20-40%.

Oral administration is the administration route, after which maximum concentration of metabolites is expected. However, after oral administration the drug rapidly undergoes metabolism to norketamine. Norketamine level is equal to 500-1000% of ketamine level. Area-under-curve (AUC) for norketamine is even higher, exceeding 1000%.

The bioavailability of orally administered ketamine is very low (ca. 16-20%); while intravenous administration results in marked increase in ketamine bioavailability, it has also many disadvantages (e.g. long-time of infusion, patient discomfort, need for surveillance).

US2007/0287753A1 discloses the use of ketamine for treating treatment-resistant or refractory depression. The only formulation tested is the intravenous infusion, and transdermal administration is contemplated as well. Intranasal administration is only generally described, including intranasal administration of a dry powder aerosol formulation comprising finely divided powder of ketamine, a dispersant and bulking agent. However, with intranasal administration ketamine to oropharyngeal area significant amounts of ketamine will be swallowed by a patient by oral route and can undergo systemic metabolism to norketamine to cause undesired side effects.

DE102007009888 discloses the use of S-ketamine in the treatment of depression, in the dosage of 0.3 to 1.0 mg/kg. Although all possible administration routes are generally mentioned, the only formulation tested is intravenous infusion, mentioned as the preferred one.

WO2013/138322 discloses the use of esketamine in the treatment of treatment-refractory or treatment-resistant depression. Test for efficacy of esketamine was described in a prophetic example with esketamine intravenous infusion.

WO2014/143646 and WO2014/152196 disclose pharmaceutical composition of esketamine in the form of the aqueous formulation of esketamine hydrochloride, preferably for nasal administration, for use in the treatment of treatment-refractory or treatment-resistant depression.

Mucoadhesive oral forms of esketamine and pharmacokinetics of esketamine after oral, intranasal and intravenous administration are described in WO2014/020155.

K. Jonkman et al., Anesthesiology 127 (4), 675-683, 10, 2017, studied on healthy volunteers the safety and feasibility of delivery of ketamine by inhalation of nebulized esketamine hydrochloride saline solution as a new route of ketamine administration. It has been found that inhaled ketamine bioavailability was reduced due to both dose-independent and dose-dependent impairment of pulmonary uptake. This was related to the high viscosity of esketamine; the viscosity of esketamine is three to four times greater than that of water. Because of this the administration via nebulization will be imprecise and non-reliable.

Singh et al., Biological Psychiatry 80:424-413, 2016, observed a rapid onset of robust antidepressant effects in patients with TRD after a 40-minute i.v. infusion of either 0.20 mg/kg or 0.40 mg/kg of esketamine. The lower dose may allow for better tolerability while maintaining efficacy.

The above illustrates the absolute medical need and importance of development of high-dose ketamine formulation that is both highly effective as well as convenient and easy to everyday self-administration by the patient including self-administration on out-patient basis to ensure high patient compliance. Such a formulation should first of all deliver therapeutic ketamine dose to the blood, should be characterized with high effectiveness, including rapid therapeutic effect and low risk of undesired effects, such as DP, due to precise dosing. Such a formulation should allow only a minimum level of systemic first-pass metabolites such as norketamine and hydroxylated metabolites, especially assure acceptable (es)ketamine to (es)norketamine ratio, both in view of avoiding reduction of ketamine level actually administered and unwanted metabolites effects.

The target was to achieve similar ketamine plasma concentration and hence similar antidepressant effect as that by Sing et al. with intravenous infusion of 0.20 mg/kg lasting 40 minutes using route of administration more convenient for a patient and producing less adverse effects.

The above problems have been solved by the present invention that provides a high-dose and stable ketamine inhalable pharmaceutical composition for use in a method of treatment of depression by pulmonary administration route in a reliable, reproducible and convenient manner, using a specific dosage regimen.

SUMMARY OF THE INVENTION

The invention provides an inhalable pharmaceutical composition comprising ketamine or a pharmaceutically acceptable salt thereof for use in a method of treatment of depression by administration of said composition to the lungs via pulmonary route of administration.

In another aspect, the invention provides ketamine or its pharmaceutically acceptable salt for use in a method of treatment of depression, wherein ketamine or its pharmaceutically acceptable salt is administered to the lungs by pulmonary route as an inhalable pharmaceutical composition.

Another object of the invention is a method of treatment of depression, which comprises administering to the lungs by pulmonary route to a human subject in need thereof an inhalable pharmaceutical composition comprising ketamine or its pharmaceutically acceptable salt.

BRIEF DESCRIPTION OF DRAWINGS

The invention will be described in more detail below, with reference to the drawing, wherein.

DETAILED DESCRIPTION OF THE INVENTION

Figure 1:
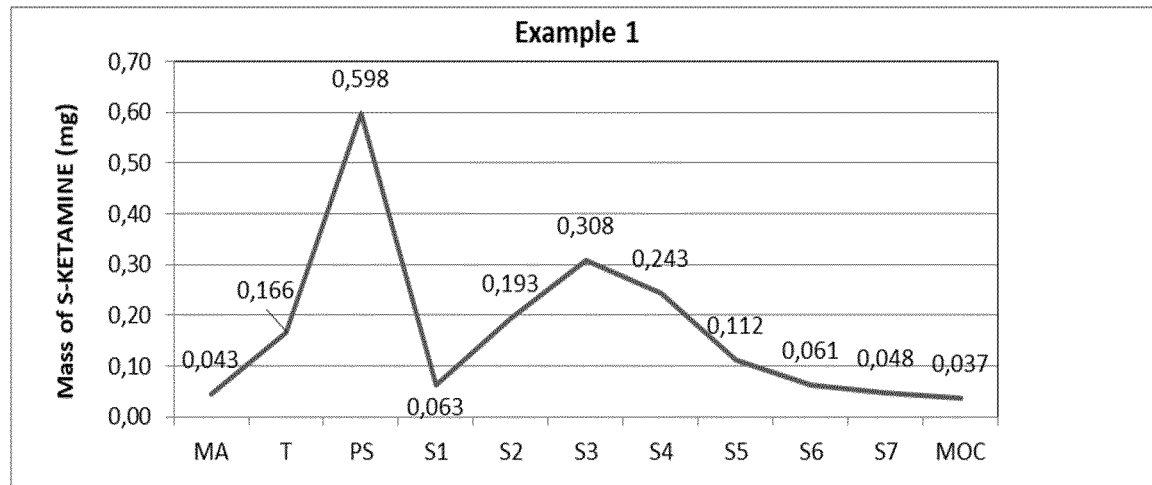
FIG. 1 presents NGI deposition data for the composition of Example 1.
Figure 1:
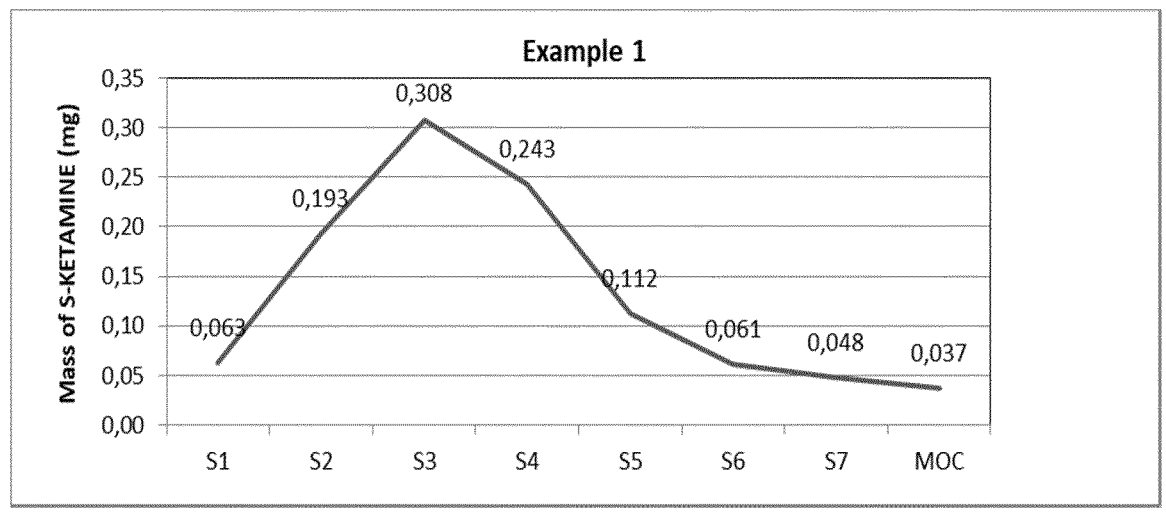

The object of the invention is an inhalable pharmaceutical composition comprising ketamine or its pharmaceutically acceptable salt for use in a method of treatment of depression by administration of said composition to the lungs, i.e. administration via pulmonary route.

Another object of the invention is a method of treatment of depression, which comprises administering by pulmonary route to a human subject in need thereof an inhalable pharmaceutical composition comprising ketamine or its pharmaceutically acceptable salt.

According to the invention, said treatment is performed in a dosage regimen that comprises cycle of multiple sequences of pulmonary administration by inhalation. Said cycle lasts from 10 days to 30 days, and in said cycle each of said multiple sequence of administration is performed in a single day. Between each of sequences of administration there is a 2 to 4 days interval without inhalation. Each of said sequence consists of multiple single dose inhalations separated by a break period lasting at least 5 minutes, and single dose inhalation consists of 1 or more puffs of the inhalable composition. Preferably there are to 2 to 4 puffs of the inhalable composition, such as 3 or 4 puffs, depending on the ketamine nominal unit dose delivered by the dry powder composition.

Said cycle can be repeated when and how needed, in accordance with the assessment and recommendations of the physician.

According to the invention, the term "ketamine" encompasses racemic ketamine and its enantiomers esketamine and arketamine, both as a free base and pharmaceutically acceptable salts thereof.

In a preferred embodiment ketamine is esketamine.

In another embodiment, ketamine is racemic ketamine.

Preferred pharmaceutically acceptable ketamine salt is hydrochloride.

In a most preferred embodiment, the composition of the invention comprises esketamine hydrochloride.

In another embodiment, the composition of the invention comprises racemic ketamine hydrochloride.

The term "medicine" as used herein can be used interchangeably with the term "medicinal product". It should be understood that "medicine" and "medicinal product" have essentially the same meaning in terms of the invention.

The invention finds the use especially in the treatment of severe types of depression such as major depressive disorder, bipolar disorder and treatment-resistant depression.

An inhalable pharmaceutical composition may be any known composition for inhalation via pulmonary route, including inhalable composition for nebulization in the form of suspension or solution in a solvent, such as an aqueous solution, and a dry powder composition for inhalation. Such composition and methods of manufacturing and delivery thereof are generally known as such.

Preferred inhalable pharmaceutical composition is a dry powder inhalable composition.

In one aspect the composition of the invention, especially dry powder composition, comprises from 2 mg to 100 mg of ketamine calculated as a free base per nominal unit dose.

In a particular embodiment, the composition for the use of the invention, especially dry powder composition, comprises from 2 mg to 60 mg of ketamine, especially 2 mg to 40 mg of ketamine, such as from 3 mg to 15 mg of ketamine, calculated as a free base, per nominal unit dose.

In another embodiment, the dry power inhalable composition for the use of the invention comprises further one or more additives selected from the group consisting of a carbohydrate bulking agent in the amount of 30 to 95% by weight and a stabilizing agent in the amount of 0.2-3% by weight, with respect to the total weight of the composition.

The composition especially dry powder composition, comprises ketamine, especially esketamine hydrochloride, having median particle diameter d50 of 1-10 µm, such as 1-8 µm, especially 3 µm, d10 of 0.2-5 µm and d90 of 3-35 µm.

Median particle size $d_{50}$ is a parameter obtained by laser diffraction technique with dry dispersion using Sympatec HELOS laser diffractometer attached with ASPIROS feeder. For measurement, raw ketamine, especially esketamine hydrochloride, is dispersed with pressure 3.0 bar in total amount of 30 mg per sample.

The composition may be a dry powder inhalable formulation for administration using dry powder inhalers. Conventional and typical dry powder inhalers can be used for this purpose.

The term "dry powder" is known for a skilled person and should be understood in a manner conventional in the art as a solid mix of particles that is fluidized when the patient inhales after actuation of the inhaler device.

The term "nominal unit dose" in accordance with the invention relates to the ketamine dose as present (loaded) in the composition that is destined for a single administration. The nominal unit dose can be a measured dose of the dry powder to be ready for the patient to take, contained in a single unit, such as a capsule or single compartment in a blister, or a dose to be taken from for delivery from the multi-dose dry powder reservoir.

The term "emitted dose" relates to the proportion of the nominal unit dose that exits/leaves the device after inhalation by a patient.

A "single dose" in the meaning used herein is to be understood as consisting of one or more "puffs" administered one just after another and is also called "inhalation event". If there are more than one "puffs" in said single dose or inhalation event, they are separated from each other merely by a short period as necessary for technical reasons to take another breath by a subject, usually few to several seconds.

The term "puff" relates to one inhalation and have the same meaning as "inhalation" as taken by a subject within one single breath.

The dry powder inhalable pharmaceutical composition or formulation for preferred use according to the invention may comprise further pharmaceutical excipients, i.e. one or more additives selected from the group consisting of a carbohydrate bulking agent (a carrier) in the amount of 30 to 95% by weight and a stabilizing agent in the amount of 0.2-3% by weight, with respect to the total weight of the composition.

Suitable carbohydrate bulking agent (a carrier) can be lactose, D-mannitol, glucose monohydrate, trehalose, especially trehalose dihydrate, erythritol, dextrose, maltose, sorbitol or xylitol. Especially convenient bulking agent is milled lactose, such as lactose monohydrate or anhydrous lactose, especially lactose monohydrate, having suitable granulometry. Suitable granulometry is defined as having $d_{50}$ 30-200 µm (Sympatec HELOS) as the main coarse fraction (especially 80 µm). Examples of suitable lactose monohydrate commercial grades are Lactohale 200 (LH200), Lactohale 100 (LH100) and Lactohale 200LP. Various types of inhalers may require appropriate selection of lactose grade most suitable for performance thereof. Such a selection is within common skills of a skilled person.

Typical amount of the bulking agent in the composition of the invention is 30-95% by weight, especially 30 to 80% by weight, with respect to the total weight of the composition.

Pharmaceutical excipients/additives include also a stabilizer (also called force control agent—FCA), i.e. a substance that reduces adhesion and cohesion. Suitable stabilizers are for example magnesium stearate, lecithin, and aminoacids, such as leucine. Especially preferred stabilizer is magnesium stearate.

Stabilizer "disturbs" the weak binding forces between the small particles and thus helps to keep the particles separated, reduces self-adhesion of small particles and also adherence to other particles in the formulation if such other particles are present, reduces the adhesion to the inner surfaces of the inhaler, as well as improves rheological properties of powder—powder flowability.

The amount of the stabilizer in the composition of the invention is 0.2-3% by weight, especially 0.8% by weight, with respect to the total weight of the composition.

Dry powder composition or formulation for preferred use according to the invention is prepared by blending in a high-shear mixer a bulking agent/carrier of suitable granulometry with a stabilizer, and then adding ketamine, especially esketamine hydrochloride, of suitable granulometry and again blending in a high-shear mixer.

Alternatively, ketamine, especially esketamine hydrochloride, of suitable granulometry is co-processed (blended) with a stabilizer in a high-shear mixer, and then the bulking agent/carrier is added and again mixed in a high-shear mixer.

The preferred composition is a dry powder formulation for administration using dry powder inhalers. Conventional and typical dry powder inhalers can be used for this purpose.

The dry powder composition or formulation may be administered by three device categories: single-unit dose inhaler in which each dose, such as in a capsule, is loaded into the device before use; a multi-dose reservoir inhaler in which a bulk supply of dry powder with plurality of doses is preloaded into the device; and a multi-unit dose inhaler in which a plurality of single doses are individually sealed in separate compartments such as in a blister cavity, and discharged each time the device is actuated. Preferred is the multi-unit dose inhaler in which a plurality of single doses are individually sealed, such as in the blister, and discharged each time the device is actuated.

In one embodiment of the use according to the invention as defined above, the dry powder composition for administration via pulmonary route is comprised in a blister with plurality of individual nominal unit doses premetered and individually sealed. One preferred example of an inhaler using such blisters is Diskus type inhaler.

In another embodiment of the use according to the invention as defined above, the dry powder composition for administration via pulmonary route is comprised in a capsule with a single nominal unit dose.

In another embodiment of the use according to the invention as defined above, the inhalable composition, especially dry powder composition, for administration of a single dose via pulmonary route is comprised in a multi-dose powder reservoir.

The composition for use according to the invention provides emitted dose of at least 1.0 mg of ketamine calculated as a free base, corresponding to 1.2 mg of ketamine hydrochloride.

Preferably, the composition for use according to the invention comprises nominal unit dose of from 2 mg to 100 mg of micronized ketamine calculated as a free base per nominal unit dose, such as 2 mg to 40 mg, such as from 2 to 20 mg, of micronized esketamine calculated as a free base per nominal unit dose.

More preferably, the composition for use according to the invention comprises nominal unit dose of 4.0 mg of ketamine, especially esketamine, corresponding to 4.6 mg of ketamine or esketamine hydrochloride.

The composition for use according to the invention provides the fraction of the dose delivered locally directly to the lungs that is at least 40%, such as from 40 to 50%, especially 40% to 60%, especially up to 85%, of the emitted unit dose.

Emitted dose is the portion of nominal unit dose that is emitted from the inhaler device and leaves the inhaler device as an aerosol and hence is available to the patient.

Only part of emitted dose reaches the lungs and thus circulating blood of a patient as the dose delivered to the lungs (also called Fine Particle Dose—FPD) or fraction delivered to the lungs (also called Fine Particle Fraction—FPF). Some part reaches gastrointestinal tract via oropharyngeal and oral routes, i.e. is swallowed, and is accessible for undesired first-part metabolism.

It has been surprisingly found that in spite of well-known problems with inhalable formulations with high doses of an active substance for pulmonary administration, the uniform and stable high-dose ketamine, especially esketamine hydrochloride inhalable composition, especially dry powder inhalable composition, can be obtained that when administered by pulmonary route provides therapeutic ketamine level in the circulating blood of a patient, i.e. at least 50 to 100 ng/ml, such as 70 to 100 ng/ml, such as 70-80 ng/ml, such as about 100 ng/ml. Therapeutic ketamine level relates to the level in the blood that is effective in the treatment of depression, especially major depressive disorder or bipolar disorder, such as treatment resistant or treatment-refractory depression, and may be dependent on the subject, gender, age, severity of the disease, the type of the inhaler, and may vary depending on whether ketamine is racemic ketamine or enantiomeric ketamine.

The fraction of the emitted dose delivered to the lungs is surprisingly high, in contrast with typical inhalable compositions wherein the standard is that only 15 to 20% of the emitted dose is delivered to the lungs.

The fraction of the emitted dose delivered locally directly to the lungs (also called Fine Particle Fraction—FPF) can be determined using well-known and conventional methods and assays. Such methods and assays include any of those described in European Pharmacopeia 9.0, Chapter 2.9.18, Preparations for inhalation; Aerodynamic assessment of fine particles for determination of Fine Particle Dose. In particular, the Next Generation Pharmaceutical Impactor (NGI) (Ph. Eur. Apparatus E) can be used to assess and control the aerodynamic particle size distribution (APSD). The NGI apparatus is as presented in FIGS. 2.9.18.-12 and 2.9.18.-13 on page 333 of European Pharmacopeia 9.0.

Emitted dose and fine particle dose and fraction (FPF and FPD) are strongly dependent on two factors i.e. on the formulation and on the device. For the device the most discriminatory factor for emitted dose is resistance. The resistance of a dry powder inhaler (DPI) is an intrinsic value which depends on the design of the inhalation channel, the metering cup and the air inlets. DPIs can be classified into four resistance groups (low, medium, medium-high, high) with respect to the inhalation flow required to produce a pressure drop of 4 kPa. This value has been chosen because it is the one recommended by pharmacopoeia for the in vitro characterization of the dose emitted from a DPI. Additionally for capsule-based DPIs can be limited by the powder retention in the capsule and device, which lead to reduction in the emitted dose.

Emitted dose testing is relatively straightforward. The device is 'fired' into a sampling apparatus that enables the capture of the measured dose on a filter. The aerodynamic particle size distribution of inhaled products is measured using the technique of multistage cascade impaction, here Next Generation Impactor (NGI). The collected quantity of active ingredient is determined further by HPLC analysis.

The inhalers are tested at a predetermined flow rate, and the pressure drop across the inhaler is 4.0 kPa in line with the Ph Eur.

Efficient particle capture is ensured by coating the particle collection surface of each of stages 1-7, as well as the MOC and the pre-separator base, with a coating substance. The central cup of the pre-separator is filled with adequate diluent.

After discharging the powder to the NGI (Number of actuations per impactor n=1 for one analysis) by opening the two-way solenoid valve for the required time at flow control which generate pressure drop across the inhaler 4 kPa the following operations are performed:

I. Stages 1 to 7 and MOC. Each stage is washed with appropriate diluent (extraction of drug substance). NGI tray loaded with the cups on a Copley Gentle Rocker is gently shaken for 10 minutes.

II. Mouthpiece adapter. Deposited inhalation powder on adapter is rinsed with appropriate diluent a volumetric flask and sonicated for 10 minutes.

III. Induction port. Deposited inhalation powder from induction port is rinsed with appropriate diluent into a volumetric flask and sonicated for 10 minutes.

IV. Preseparator. Deposited inhalation powder from these component is rinsed with appropriate diluent into a volumetric flask and sonicated for 10 minutes.

Finally collected samples from each stage of impactor are filtered analyzed by high-performance liquid chromatography Composition of for use according to the invention, especially dry powder composition, has an appropriate ketamine, in particular esketamine, pharmacokinetics profile that enables achievement of approximately 50 to 100 ng/ml of the ketamine plasma concentration over 40 minutes after pulmonary administration directly to the lungs by inhalation. Said plasma concentration corresponds to antidepressive effect. Maintaining this concentration over time mimics 40-minute intravenous infusion known to be effective in depression and well-tolerated.

Preferably, in accordance with the invention said treatment cycle lasts 12 to 14 days and comprises 4 sequences of administration separated by 3 to 4 day intervals.

Preferably, in the use according to the invention, esketamine, especially esketamine hydrochloride, is self-administered pulmonary by a patient by inhalation of an inhalable composition or formulation, especially dry powder inhalable esketamine composition or formulation in a sequence lasting 30 minutes and consisting of 3 single doses (inhalation events), each inhalation event consisting of 3 or 4 puffs, wherein each puff corresponds to esketamine free base nominal dose of 4 mg in the composition, especially dry powder composition. Such a composition is described in Example 2 below. Between such each inhalation event (single dose) there is provided a break period without any inhalation, preferably there are two equal breaks lasting about 15 minutes, i.e. first single dose is administered at time 0, second single dose is administered after about 15 minutes and the third single dose is administered at 30 minute. Such a sequence allows to obtain esketamine plasma concentration profile that provides plasma concentration at the level having antidepressant effect, as known from prior art tests of intravenous infusions.

It has been found that esketamine inhalable composition, especially dry powder inhalable composition, was tolerated within the whole treatment cycle and the number and intensity of adverse effects diminished within the treatment cycle, i.e. was lower after each subsequent treatment sequence than in the preceding sequence.

The present invention will now be with reference to the accompanying examples, which are not intended to be limiting.

EXAMPLES

General Manufacturing Procedure of Dry Powder Inhalable Composition

A sum of lactose monohydrate and magnesium stearate are sieved through 0.25 mm mesh and mixed in high-shear mixer for 3 minutes. Obtained mixture is sieved with active substance through 0.5 mm mesh and mixed in high-shear mixer for 5 minutes.

To eliminate electrostatic charges, antistatic PE bags are used during the process.

Vacuum Filling Process (Blisters):

Vacuum-drum technology dose forming process is used for blister filling. The blister cavity is in volume range of 15 to 45 mm$^3$ (especially ca. 30 mm$^3$). Powder which is filled into cavity is in amount of 10-30 mg (especially 23 mg).

During process parameters of vacuum-drum device are:
Vacuum pressure: −0-500 mBar, especially 50-400 mBar
Fluidization pressure: −0.1−−0.4 Bar
Fluidization time: 50-2000 ms, especially 50-300 ms
Filling time: 50-700 ms, especially 50-400 ms
Sealing time: 100-600 ms
Sealing tests of filled blisters are performed under vacuum.

Finally, the blister strips are coiled into the medical device.

Filling Process (Capsules):

Capsules to be filled are placed in the sockets closed ends down. Powder is discharged from the dosator and comes directly to the capsules. The powder with which the capsules are to be filled is placed in the dosator, may be tamped and discharged into the capsules.

During the process parameters of capsule filling device are:
Rotation: 1-70 rpm
Tamping high: 1-10 mm
Dosator high: 1-250 mm Finally, the filled capsules are mounted into the medical device.

Ketamine Dry Inhalation Powder for Blisters and Capsules

The following compositions has been prepared in accordance with the above general procedure in the scale of 0.9 kg.

Example 1

| Component | Amount (mg/unit) |
|---|---|
| Esketamine hydrochloride | 3.45 (corresponds to 2.99 mg esketamine) |
| Lactose monohydrate LH200 LP | 19.16 |
| Magnesium stearate | 0.39 |

Example 2

| Component | Amount (mg/unit) |
|---|---|
| Esketamine hydrochloride | 4.61 (corresponds to 4 mg esketamine) |
| Lactose monohydrate LH200 LP | 18.20 |
| Maanesium stearate | 0.18 |

Example 3

| Component | Amount (mg/unit) |
|---|---|
| Esketamine hydrochloride | 5.06 (corresponds to 4.39 mg esketamine) |
| Lactose monohydrate LH200 LP | 17.581 |
| Magnesium stearate | 0.359 |

The compositions have been found uniform in accordance with requirements of Ph.Eur.2.9.40. Average esketamine hydrochloride content (n=10) was in the range 92.5%-107.5% of nominal dose.

The process has been found scalable to the scale of 1.8 kg.

Aerodynamic Particle Size Distribution (APSD) test of the compositions of the Examples 1, 2 and 3 of the invention.

The compositions of Examples 1, 2 and 3 of the invention have been tested using the Next Generation Pharmaceutical Impactor (NGI) (Ph. Eur. Apparatus E) in accordance with the procedure for powder inhalers.

Figure 2:
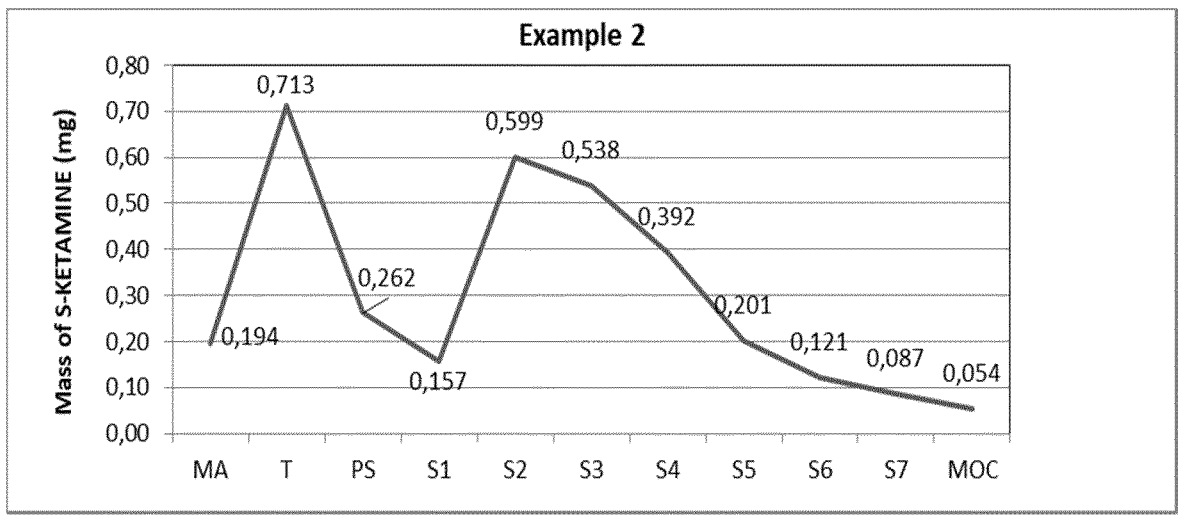
FIG. 2 presents NGI deposition data for the composition of Example 2.
Figure 2:
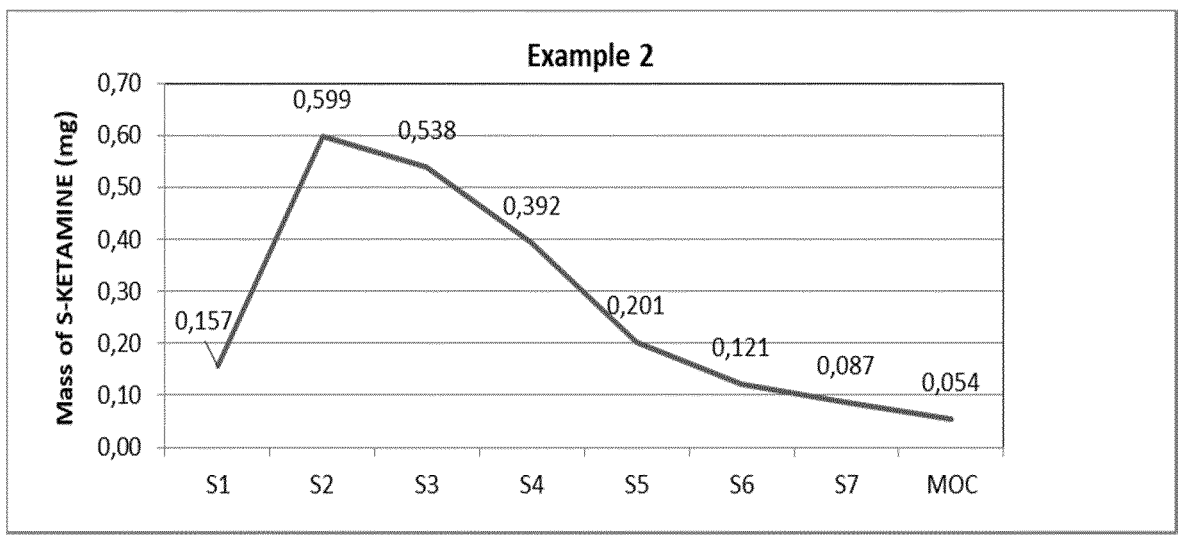
Figure 3:
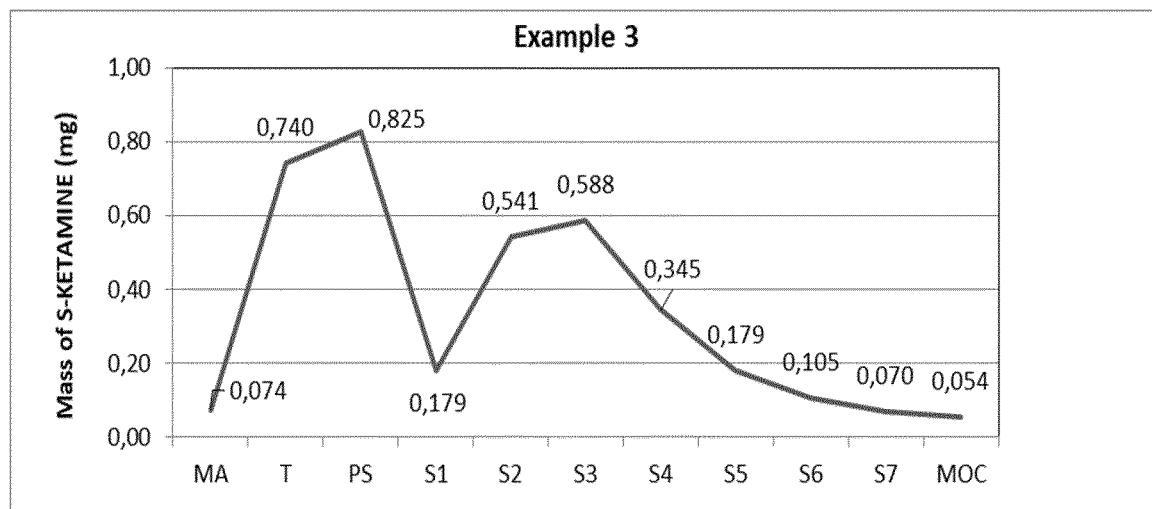
FIG. 3 presents NGI deposition data for the composition of Example 3.
Figure 3:
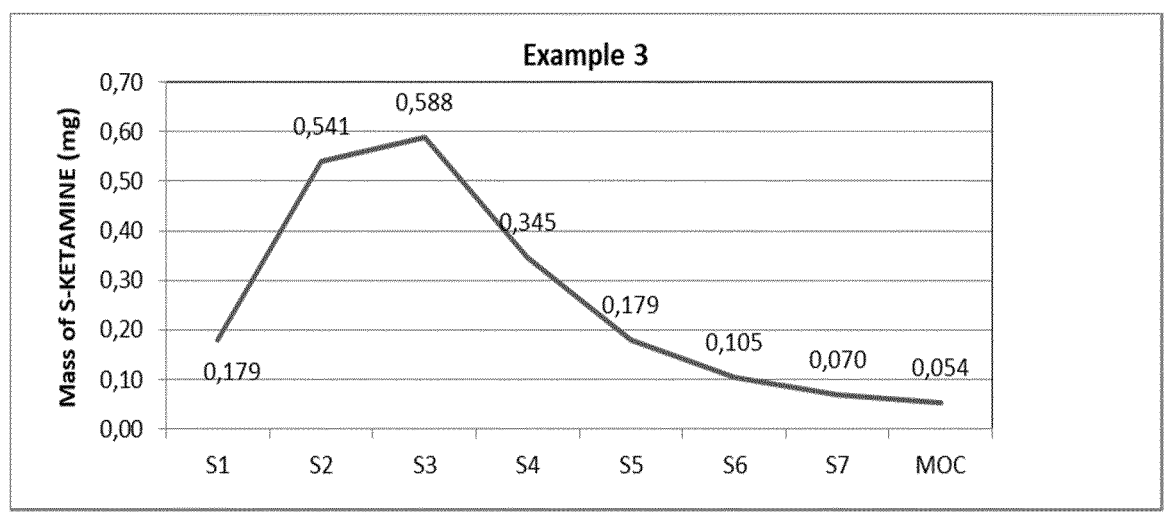
Figure 4:
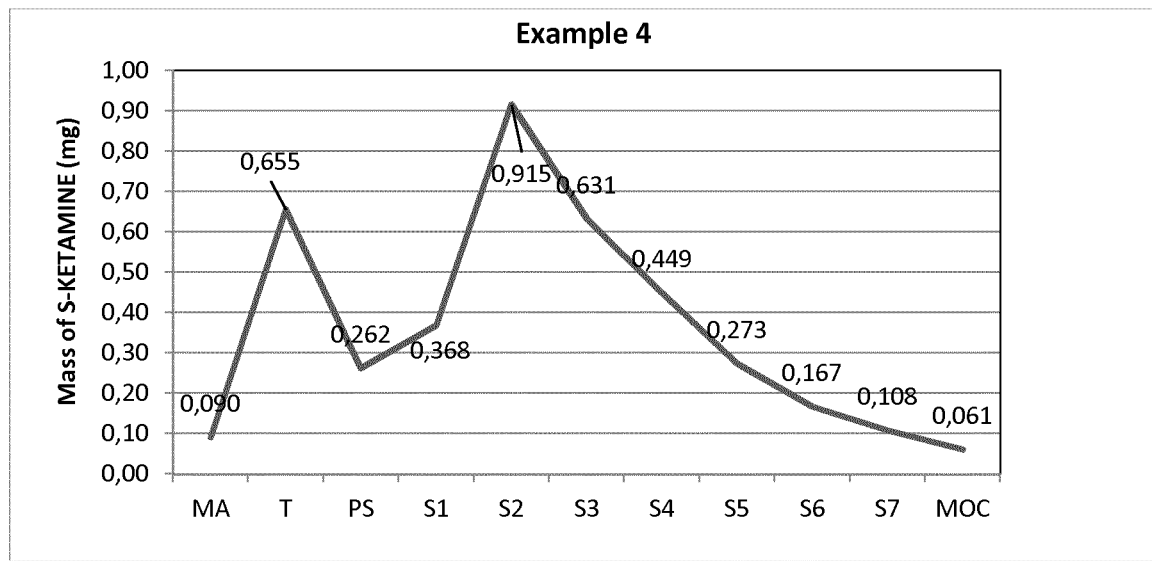
FIG. 4 presents NGI deposition data for the composition of Example 4.
Figure 4:
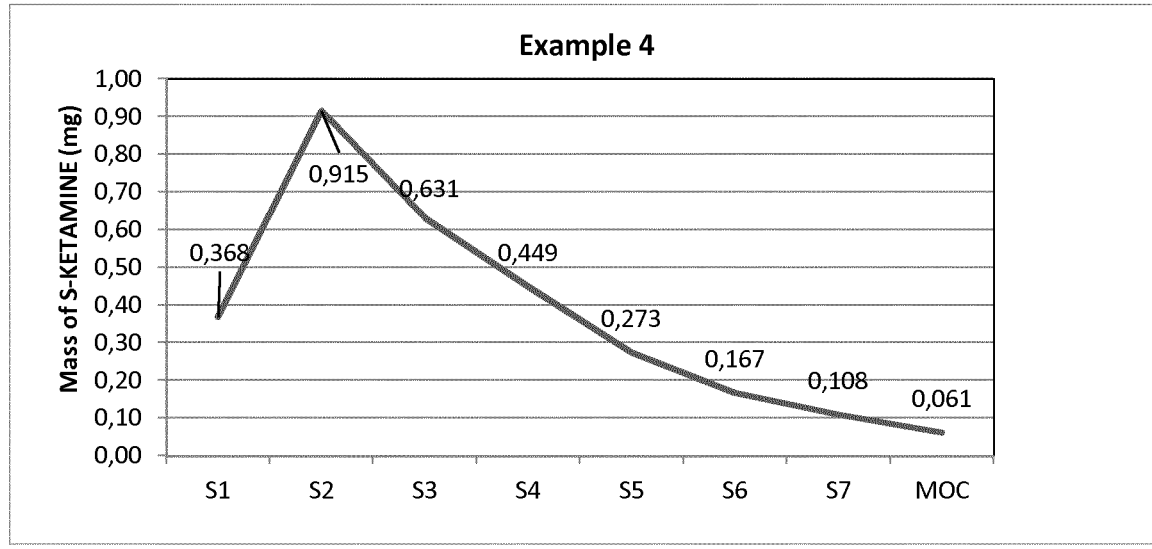

The results of the tests are presented in Table 1 below and in FIG. 1 (Example 1), FIG. 2 (Example 2) and FIG. 3 (Example 3) of the drawing, wherein upper diagrams present APSD data for the whole NGI and bottom diagrams present APSD data for stages 1-7 and MOC. The following abbreviations are used for the results of the tests:

MA—mouth adapter
T—induction port
PS—Pre-separator
S1-S7—stages of NGI
MOC—micro-orifice collector
ISM—Impactor sized mass; mass entering the impactor excluding non-sizing portions
MMAD (μm)—mass median aerodynamic diameter. Defined as the diameter at which 50% of the particles by mass are larger and 50% are smaller.
GSD—geometric standard deviation. Measure of the spread of an aerodynamic particle size distribution
FPF—fine particle fraction (%)
FPD—fine particle dose

TABLE 1

| NGI deposition data | | | |
|---|---|---|---|
| Example No | 1 | 2 | 3 |
| MA [mg] | 0.043 | 0.194 | 0.074 |
| T | 0.166 | 0.713 | 0.740 |
| PS | 0.598 | 0.262 | 0.825 |
| S1 | 0.063 | 0.157 | 0.179 |
| S2 | 0.193 | 0.599 | 0.541 |
| S3 | 0.308 | 0.538 | 0.588 |
| S4 | 0.243 | 0.392 | 0.345 |
| S5 | 0.112 | 0.201 | 0.179 |
| S6 | 0.061 | 0.121 | 0.105 |
| S7 | 0.048 | 0.087 | 0.070 |
| MOC | 0.037 | 0.054 | 0.054 |
| ISM (mg) | 1.00 | 1.99 | 1.88 |
| Total Mass on Impactor (mg) | 1.07 | 2.15 | 2.06 |
| Total Mass on System (mg) | 1.87 | 3.32 | 3.70 |
| Mass on Impactor/Actuation (mg) | 1.07 | 2.15 | 2.06 |
| Mass on System/Actuation (mg) | 1.87 | 3.32 | 3.70 |
| FPD ≤5.0 mcm (mg) esketamine | 1.0 | 1.7 | 1.6 |
| FPF ≤5.0 mcm (%) | 49.0 | 51.0 | 44.0 |
| MMAD (mcm) | 2.6 | 2.9 | 3.0 |
| GSD | 1.8 | 1.8 | 1.8 |

The obtained results showed a product with expected quality attributes. The composition of the invention demonstrated appropriate homogeneity and a very high level of fine particle fractions, with:

FPF>49%, FPD 1.0 mg; and emitted dose: 2.3 mg, for Example 1
FPF>47%, FPD: 1.7 mg; and emitted dose: 3.6 mg, for Example 2, and
FPF>44%, FPD: 1.6 mg; and emitted dose: 3.9 mg, for Example 3.

Esketamine Dry Inhalation Powder for Capsules

The following compositions has been prepared in accordance with the above general procedure in the scale of 0.9 kg.

Example 4

| Component | Amount (mg/unit) |
|---|---|
| Esketamine hydrochloride | 5.00 (corresponds to 4.34 mg esketamine) |
| Lactose monohydrate LH200 LP | 19.8 |
| Magnesium stearate | 0.2 |

Example 5

| Component | Amount (mg/unit) |
|---|---|
| Esketamine hydrochloride | 10.00 (corresponds to 8.67 mg esketamine) |
| Lactose monohydrate LH200 LP | 39.6 |
| Magnesium stearate | 0.4 |

Example 6

| Component | Amount (mg/unit) |
|---|---|
| Esketamine hydrochloride | 20.00 (corresponds to 17.34 mg esketamine) |
| Lactose monohydrate LH200 LP | 79.2 |
| Magnesium stearate | 0.8 |

Aerodynamic Particle Size Distribution (APSD) test of the compositions of Examples 4, 5 and 6 of the invention.

The compositions of Examples 4, 5 and 6 of the invention have been tested using the Next Generation Pharmaceutical Impactor (NGI) (Ph. Eur. Apparatus E) in accordance with the procedure for powder inhalers.

Figure 5:
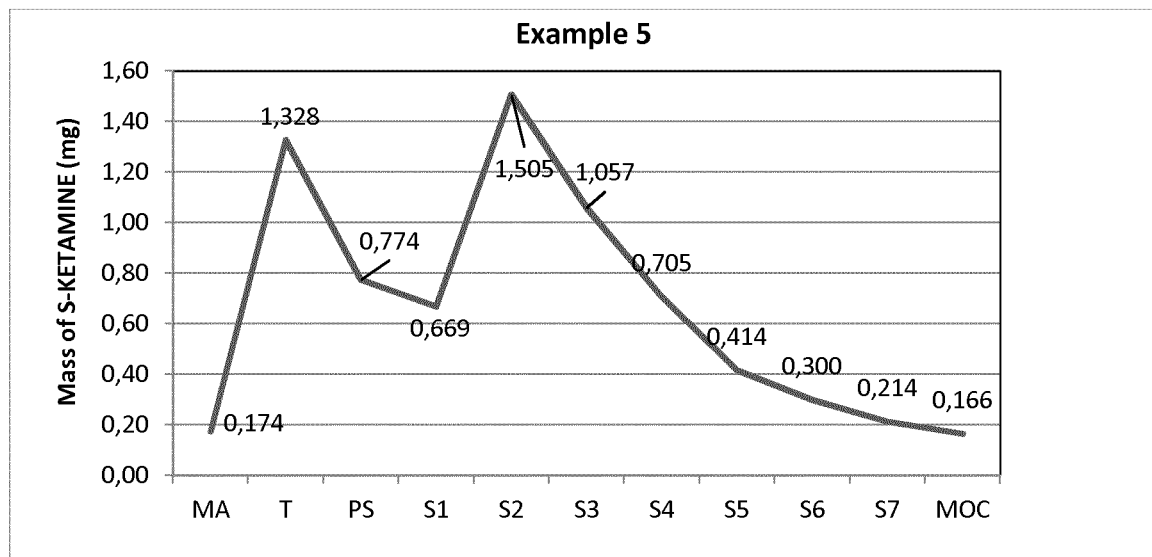
FIG. 5 presents NGI deposition data for the composition of Example 5.
Figure 5:
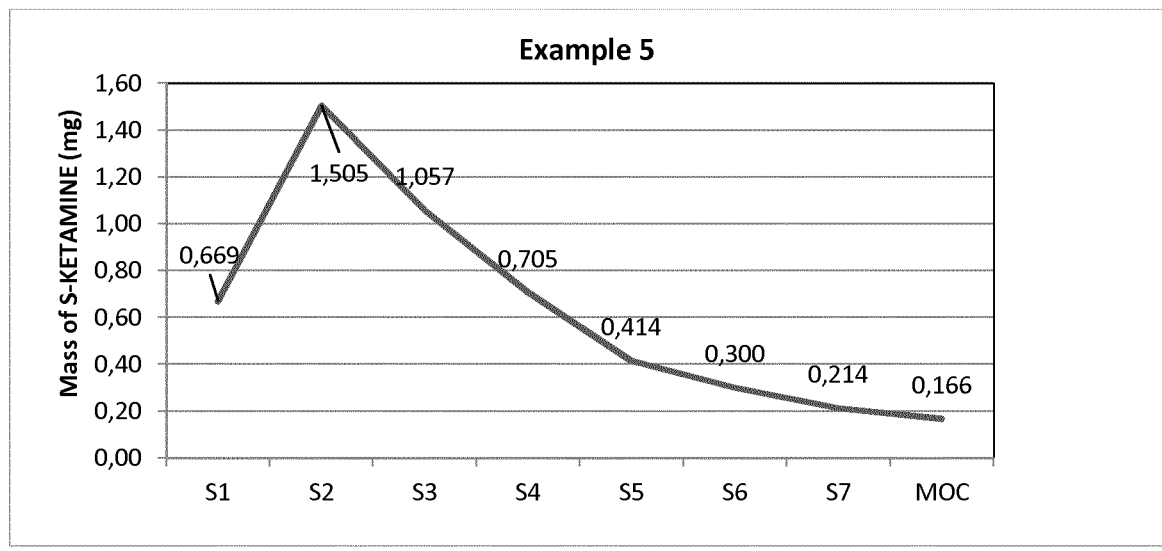
Figure 6:
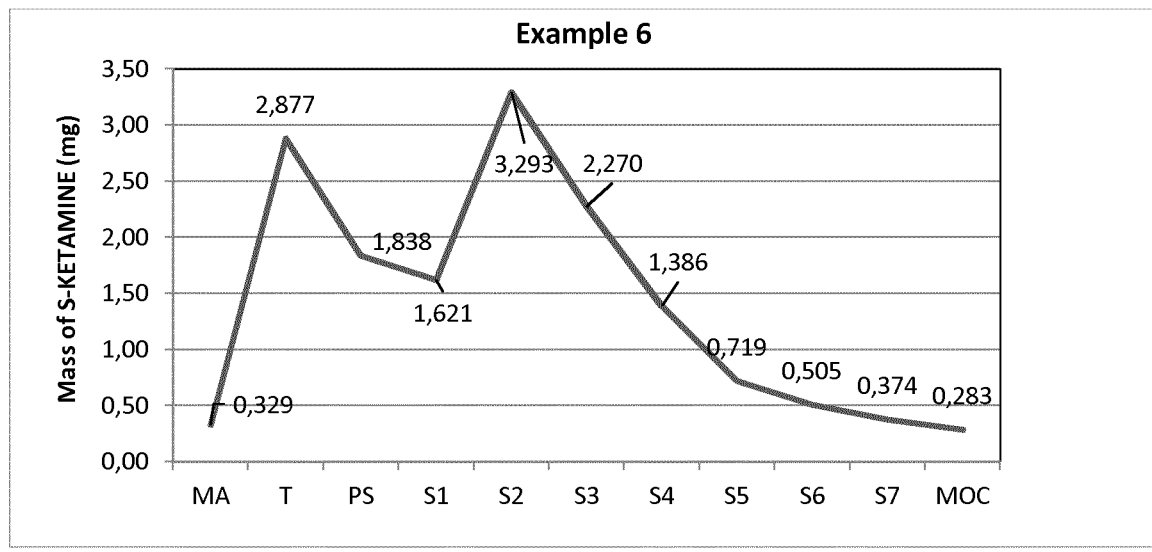
FIG. 6 presents NGI deposition data for the composition of Example 6.
Figure 6:
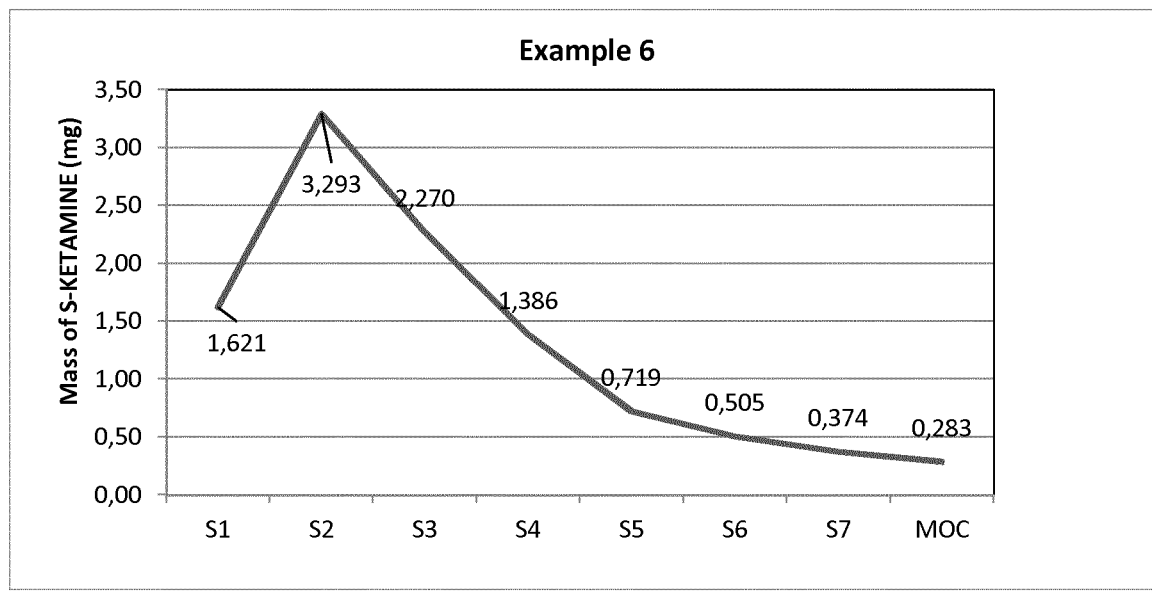

The results of the tests are presented in Table 2 below and in Figures (Example 4), FIG. 5 (Example 5) and FIG. 6 (Example 6) of the drawing, wherein higher diagrams present APSD data for the whole NGI and lower diagrams present APSD data stages 1-7 and MOC.

TABLE 2

| NGI deposition data | | | |
|---|---|---|---|
| Example No | 4 | 5 | 6 |
| MA [mg] | 0.090 | 0.174 | 0.329 |
| T | 0.655 | 1.328 | 2.877 |

TABLE 2-continued

NGI deposition data

| Example No | 4 | 5 | 6 |
|---|---|---|---|
| PS | 0.262 | 0.774 | 1.838 |
| S1 | 0.368 | 0.669 | 1.621 |
| S2 | 0.915 | 1.505 | 3.293 |
| S3 | 0.631 | 1.057 | 2.270 |
| S4 | 0.449 | 0.705 | 1.386 |
| S5 | 0.273 | 0.414 | 0.719 |
| S6 | 0.167 | 0.300 | 0.505 |
| S7 | 0.108 | 0.214 | 0.374 |
| MOC | 0.061 | 0.166 | 0.283 |
| ISM (mg) | 2.61 | 4.36 | 8.83 |
| Total Mass on Impactor (mg) | 2.97 | 5.03 | 10.45 |
| Total Mass on System (mg) | 3.98 | 7.30 | 15.49 |
| Mass on Impactor/Actuation (mg) | 2.97 | 5.03 | 10.45 |
| Mass on System/Actuation (mg) | 3.98 | 7.30 | 15.49 |
| FPD ≤5.0 mcm (mg) esketamine | 2.4 | 3.9 | 7.9 |
| FPF ≤5.0 mcm (%) | 59 | 54 | 51 |
| MMAD (mcm) | 3.0 | 3.0 | 3.2 |
| GSD | 1.9 | 1.9 | 2.6 |

The obtained results showed a product with expected quality attributes. The invented formulation demonstrated appropriate homogeneity and a very high level of fine particle fractions, with:

FPF>59%, FPD 2.4 mg; emitted dose: 4.2 mg, for Example 4

FPF>54%, FPD: 3.9 mg; emitted dose: 7.1 mg, for Example 5, and

FPF>51%, FPD: 7.9 mg; emitted dose: 16.5 mg, for Example 6.

The dry powder pharmaceutical composition of the invention provided emitted esketamine hydrochloride dose at the level up to 97%, such as up to 85% of the nominal dose and at least 40% of fine particle fraction (fraction delivered to the lungs) for emitted esketamine dose.

Example 7

Pharmacokinetics of Inhaled Esketamine Composition Dry Powder in Healthy Volunteers—Clinical Study Esketamine hydrochloride dry powder formulation of Example 2 was administered to healthy volunteers pulmonary, i.e. directly to the lungs using dry powder inhaler (DPI) (by self-administration), under supervision of medical personnel.

One puff of dry powder formulation contained 4.6 mg of esketamine hydrochloride, corresponding to 4 mg of esketamine free base and excipients 18.22 mg of lactose monohydrate and 0.18 mg of magnesium stearate.

A single dose was an inhalation events consisting of 1 to 6 puffs, i.e. 4 to 24 mg of esketamine free base nominal dose.

In part A of the study, designed as a one-centre single ascending dose, the medicine was delivered in a single dose once in one day (up to 6 consecutive puffs) to 18 healthy volunteer subjects. Subjects were divided into 6 cohorts, cohorts receiving 1, 2, 3, 4, 5 or 6 puffs in a single dose (inhalation event), respectively. Collection of blood samples for determination of esketamine and esnorketamine metabolite concentration and calculation of pharmacokinetic parameters was performed for 24 hours following the start of the test in the administration day. The aim of the study was to determine the amount of puffs in an inhalation event needed to obtain plasma concentration similar to that sufficient to achieve antidepressant effect as for 0.20 mg/kg 40 minutes intravenous infusion. It can be predicted on the basis of literature data that this corresponds to concentration at 40 min of infusion between about 60 to 100 ng/ml. It was also the aim to determine the number of puffs that allow to avoid a sharp peak of plasma concentration that is considered an important factor inducing adverse psychomimetic and dissociative effects.

Figure 7:
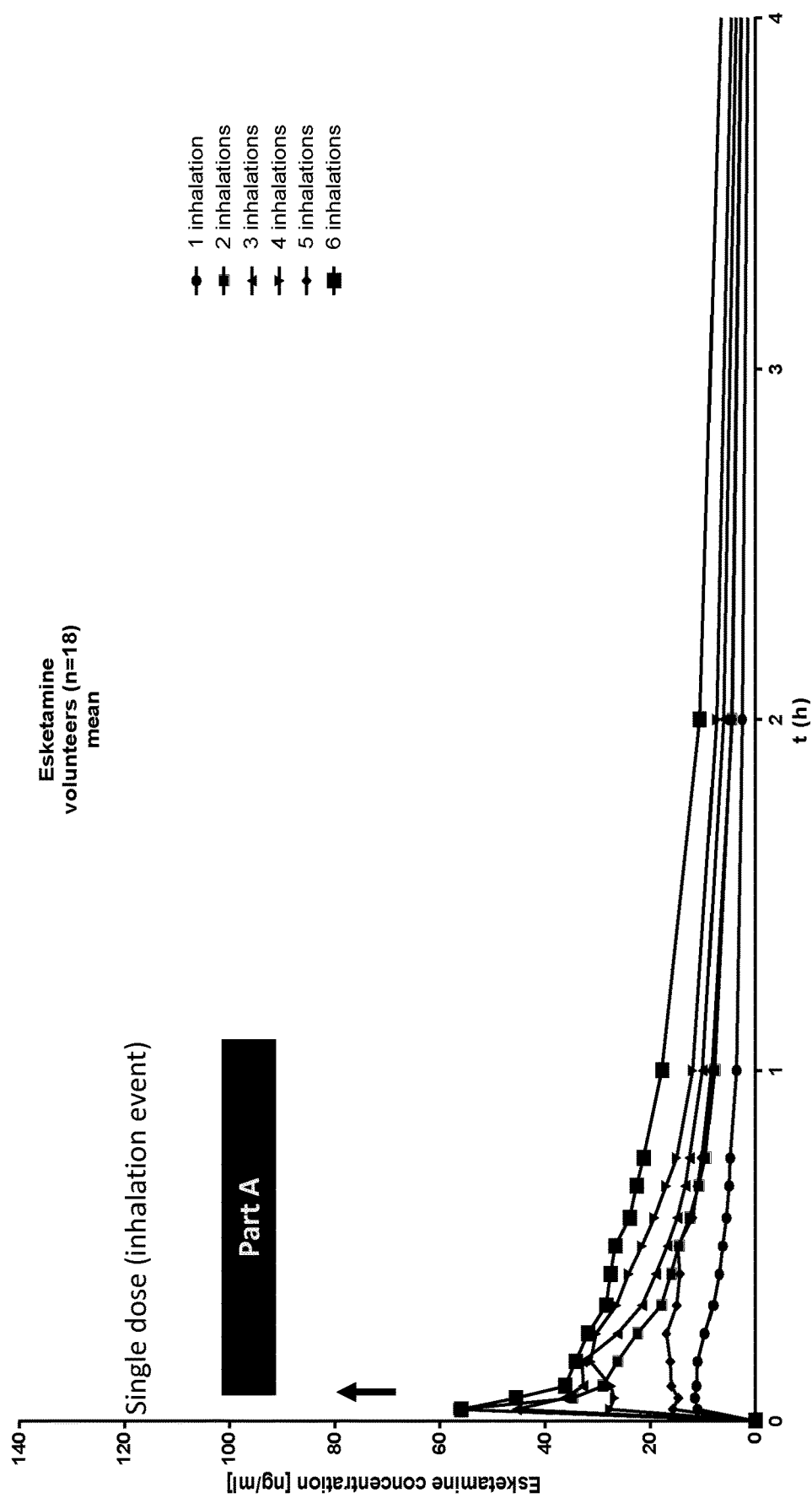
FIG. 7 shows esketamine plasma concentration vs time after administration of various single doses of dry powder composition of Example 2 in Part A of the study.

The results of the part A of the test are presented on FIG. 7 that shows esketamine plasma concentration over time after administration of various single doses of dry powder composition of Example 2. As it can be seen, the number of puffs that allows to obtain plasma esketamine concentration sufficient for antidepressant effect and without sharp peak of said concentration was determined to be 1 to 4 puffs, corresponding to 4 to 16 mg of esketamine free base nominal dose.

Therefore, a single dose (inhalation event) consisting of 1, 2, 3 or 4 puffs was selected for the next Part B of the study.

In part B of the study the composition of Example 2 was administered to 12 healthy volunteer subjects divided into 4 cohorts in four different single doses each cohort (i.e. each single dose consisting of 1, 2, 3 or 4 puffs, respectively) in one day in the administration sequence consisting of three administrations of single dose (inhalation event) in the period of 30 minutes, Between inhalation events there were 15 minutes break periods, i.e. first single dose was administered at 0 min., second single dose was administered at 15 min, and third single dose was administered at 30 min.

Collection of blood samples for determination of esketamine and esnorketamine metabolite concentration and calculation of pharmacokinetic parameters was performed for 24 hours following the start of the test in the administration day. The aim of Part B of the study was to investigate pharmacokinetic properties of esketamine following different dosing schemes in healthy subjects and determine the scheme that enables achievement of the appropriate plasma concentration over time to mimic the 40-minute intravenous infusion.

Figure 8:
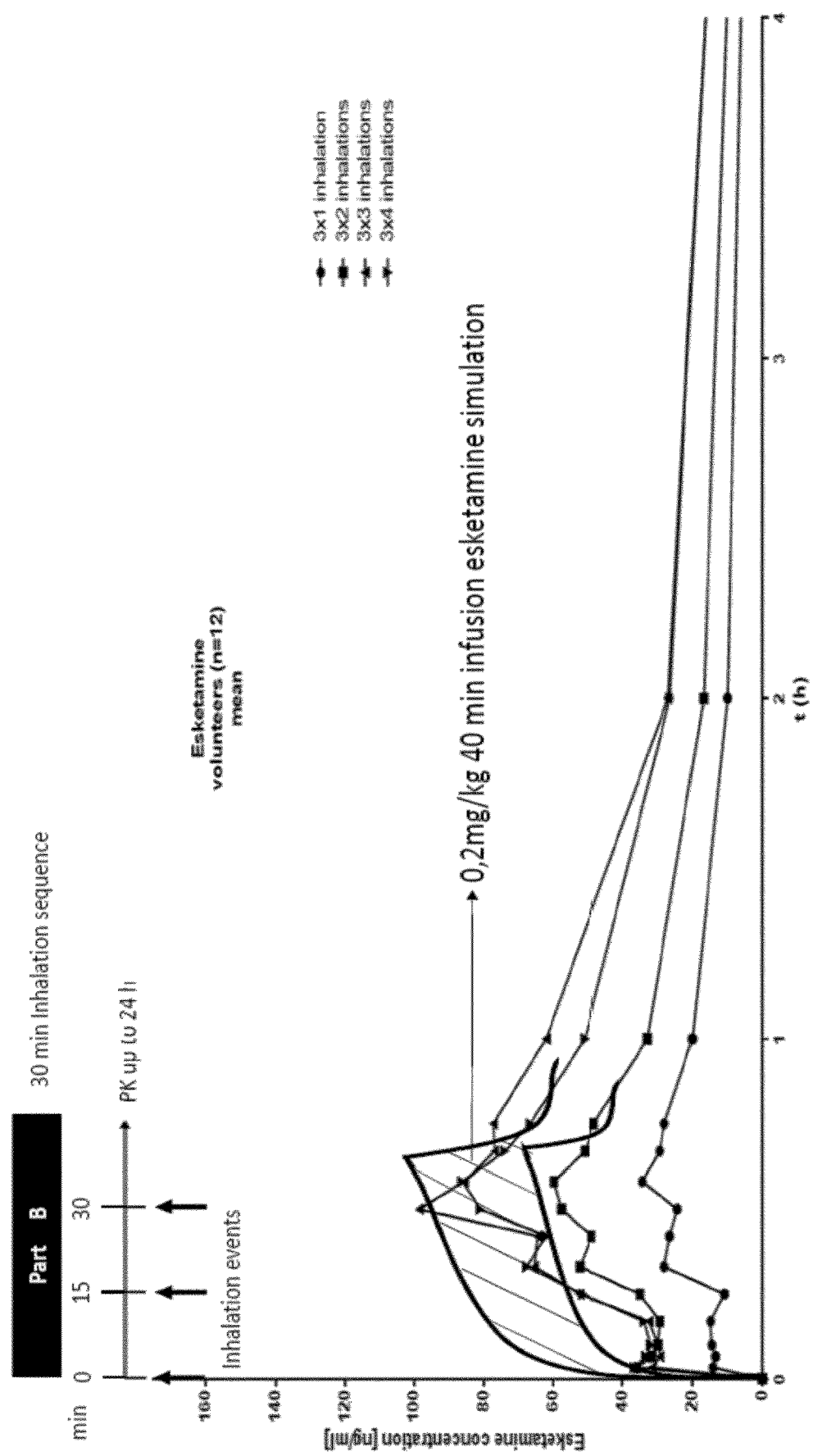
FIG. 8 shows esketamine plasma concentration vs time after administration of a sequence of single doses of dry powder composition of Example 2 in Part B of the study.
Figure 9A:
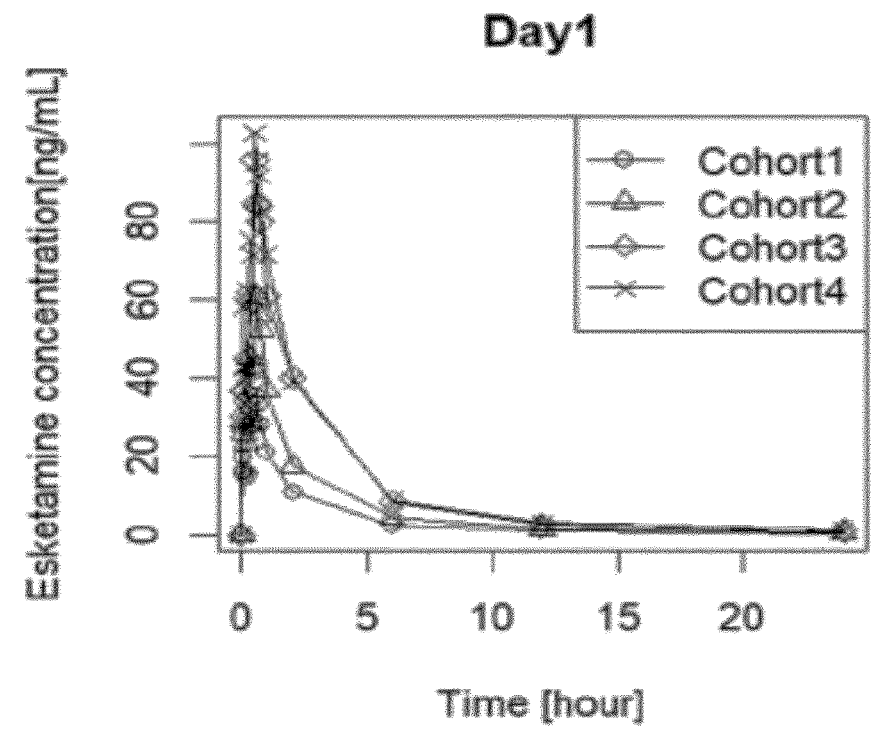
FIGS. 9A to 9D show esketamine plasma concentration vs time after administration on Day 1, Day 4, Day 8 and Day 11, respectively, in a cycle of administrations of sequences of single doses of dry powder composition of Example 2 in Part C of the study.
Figure 9B:
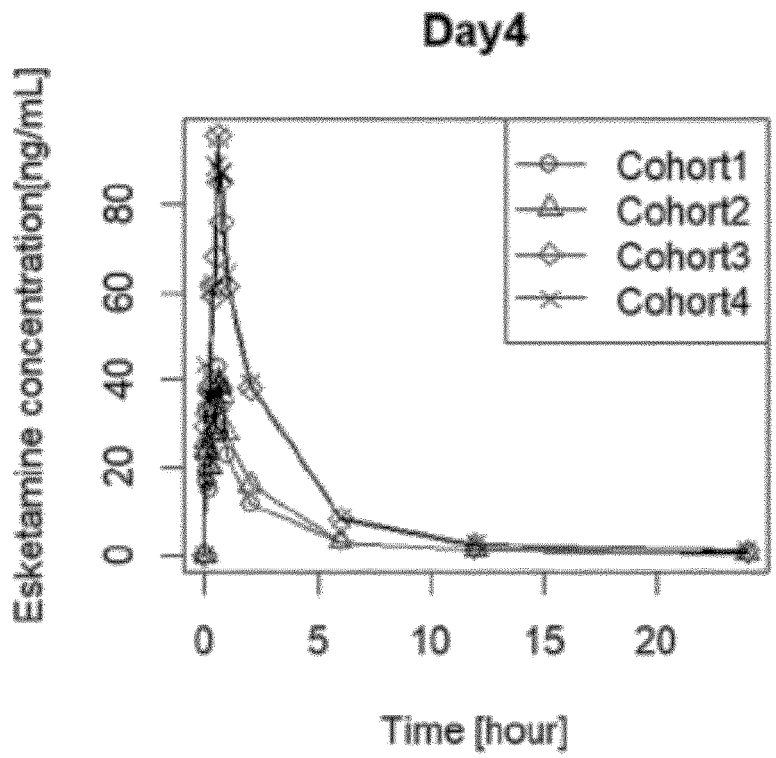
Figure 9C:
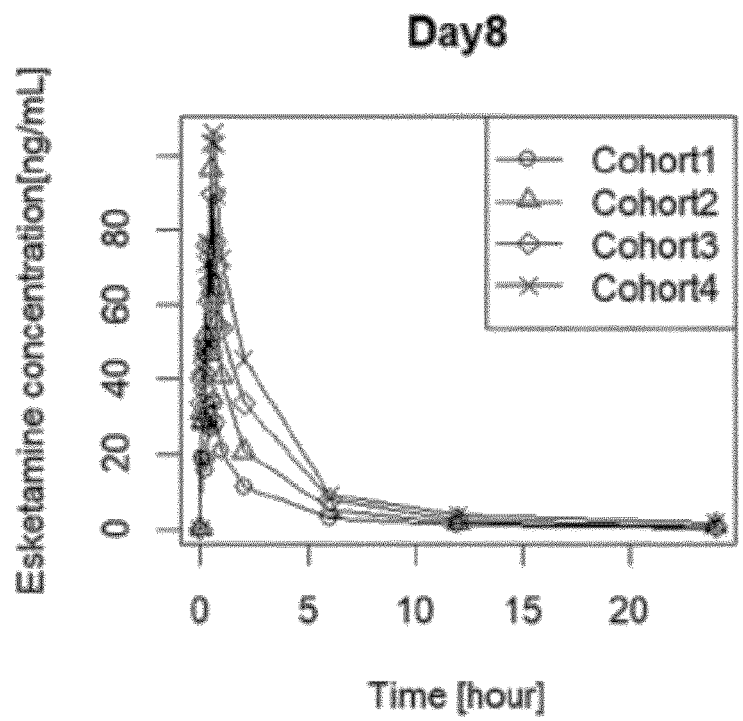
Figure 9D:
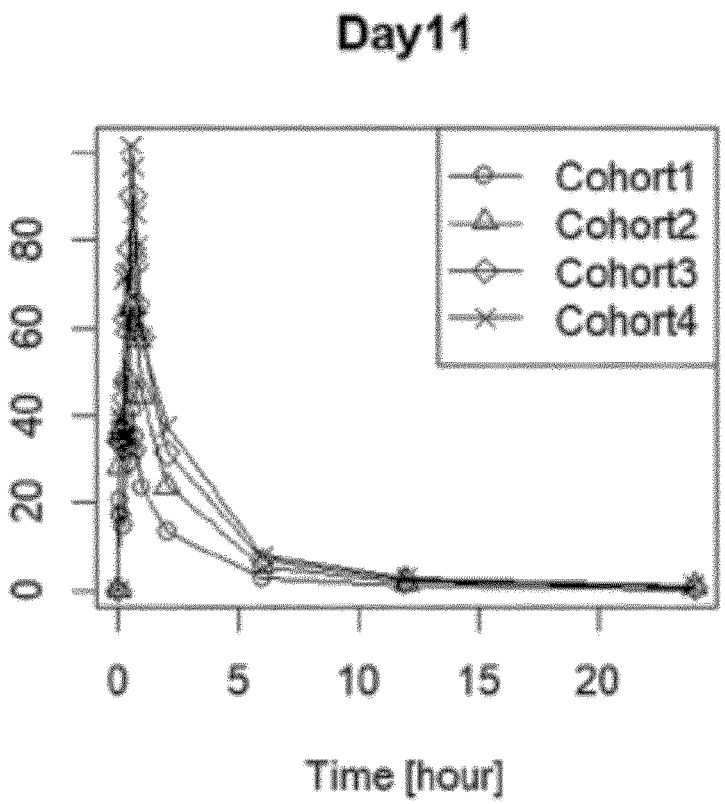

The results of the part B of the test are presented on FIG. 8 that shows esketamine plasma concentration over time after administration of various single doses of dry powder composition of Example 2 in a sequence of 3 administrations of single doses during 30 minutes. FIG. 8 shows also (the area between two bold black lines) a simulation of esketamine plasma concentration after 0.2 mg/kg 40 minutes i.v. infusion.

As it can be seen from FIG. 8, sequence of administration of 3 single doses consisting of 3 or 4 puffs allowed to obtain plasma concentration profile mimicking quite well esketamine intravenous infusion at the level corresponding to antidepressant effect.

In Part C of the study, the composition of Example 2 was administered to 33 healthy volunteers divided into 4 cohorts in a cycle consisting of 4 sequences of administration, each performed one single day, separated with 3 to 4 day intervals. Sequences were administered on Day 1, Day 4, Day 8 and Day 11. Each sequence of administration consisted of four different single doses for each respective cohort (1, 2, 3 or 4 puffs) one day in the administration sequence consisting of three administrations of single dose (inhalation event) in the period of 30 minutes, such as in Part B. Between inhalation events there were 15 minutes break periods, i.e. first single dose was administered at 0 min, second single dose was administered at 15 min, and third single dose was administered at 30 min.

Collection of blood samples for determination of esketamine and esnorketamine metabolite concentration and calculation of pharmacokinetic parameters was performed for 24 hours following the start of the test in the administration day.

The results of the part C of the study are presented on FIGS. 9A to 9D that show esketamine plasma concentration over time in a treatment cycle, i.e. on Day 1, Day 4, Day 8 and Day 11.

Figure 10:
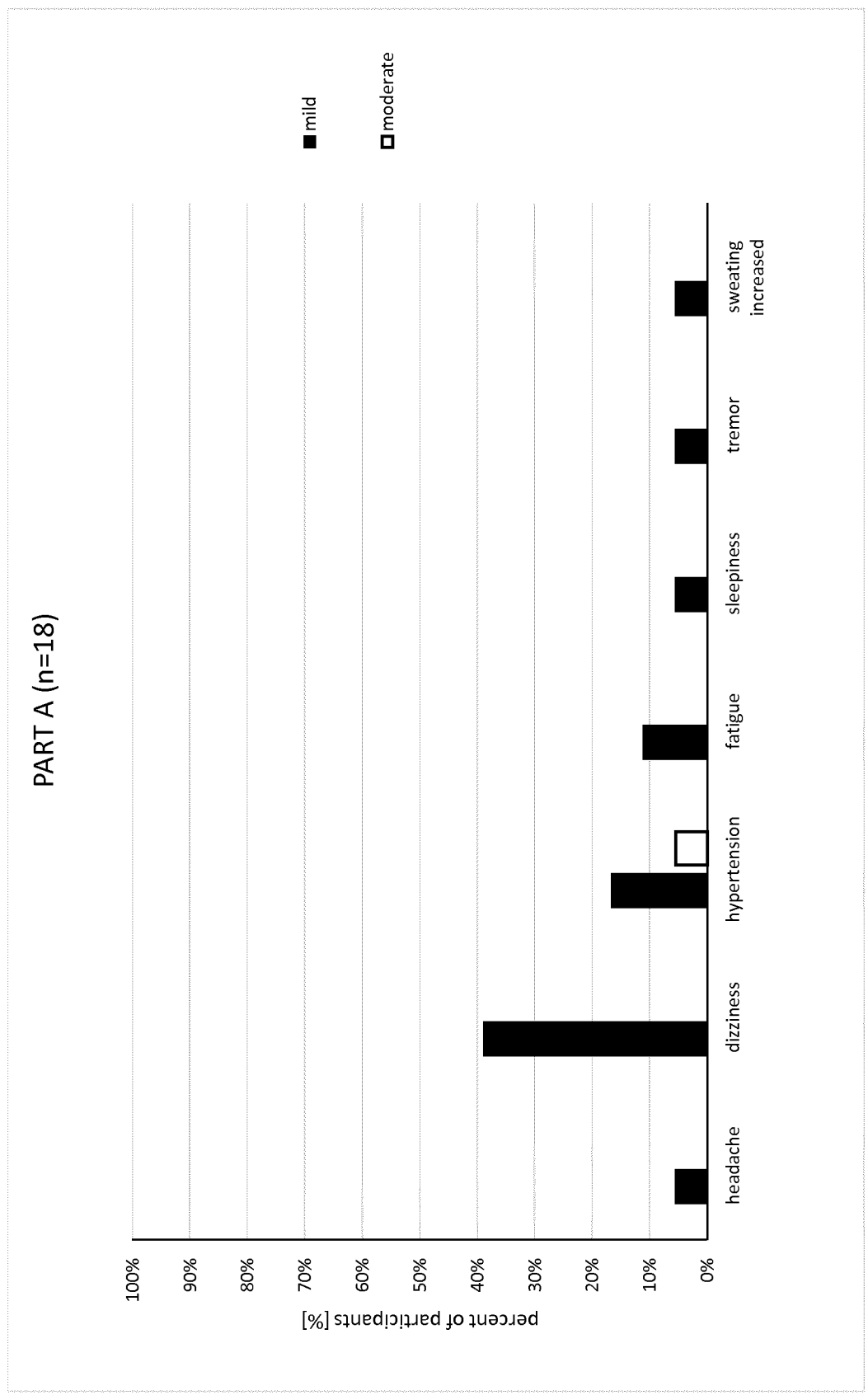
FIG. 10 presents adverse effect distribution after administration of dry powder composition of Example 2 in Part A of the study.
Figure 11:
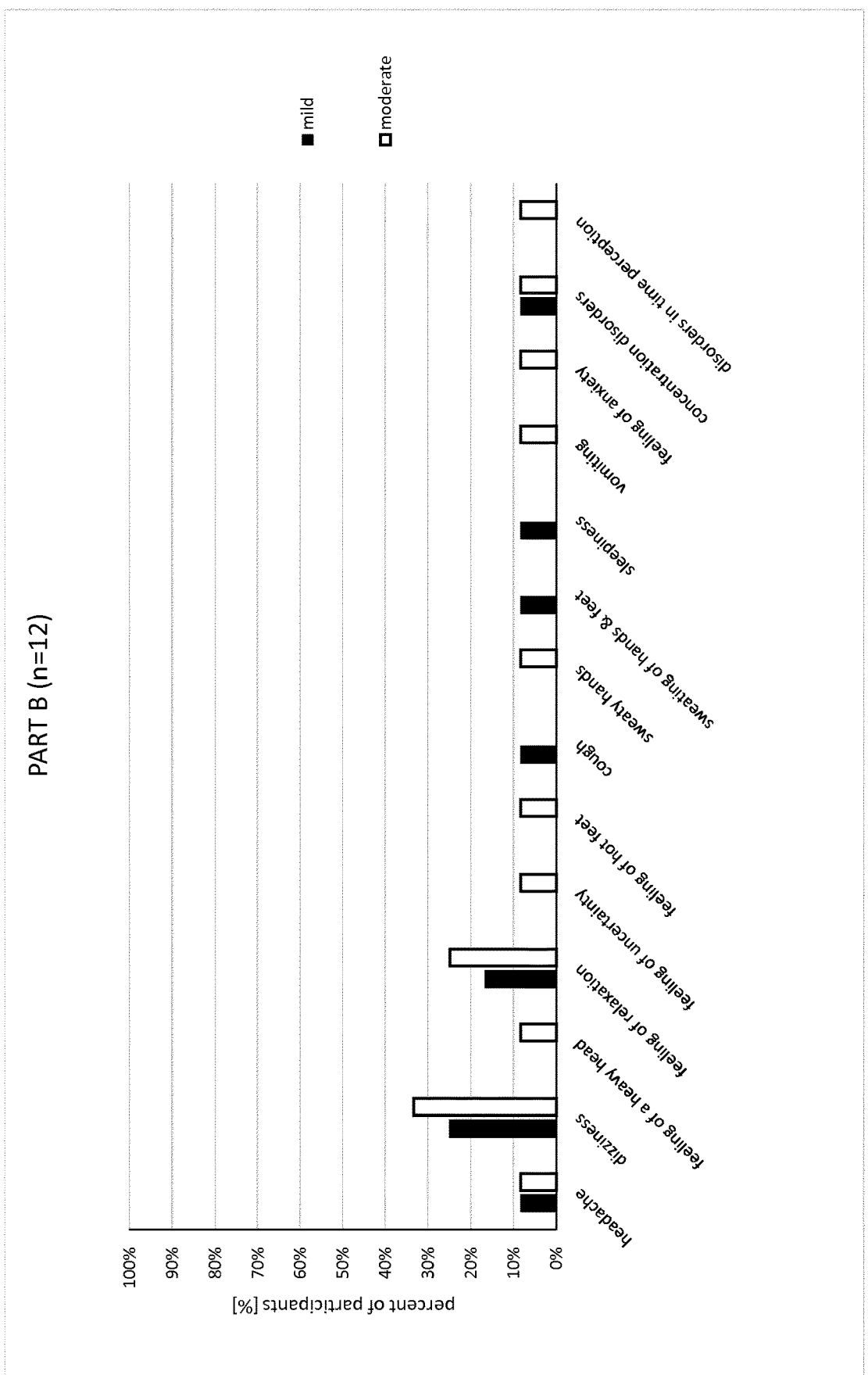
FIG. 11 presents adverse effect distribution after administration of dry powder composition of Example 2 in Part B of the study.
Figure 12A:
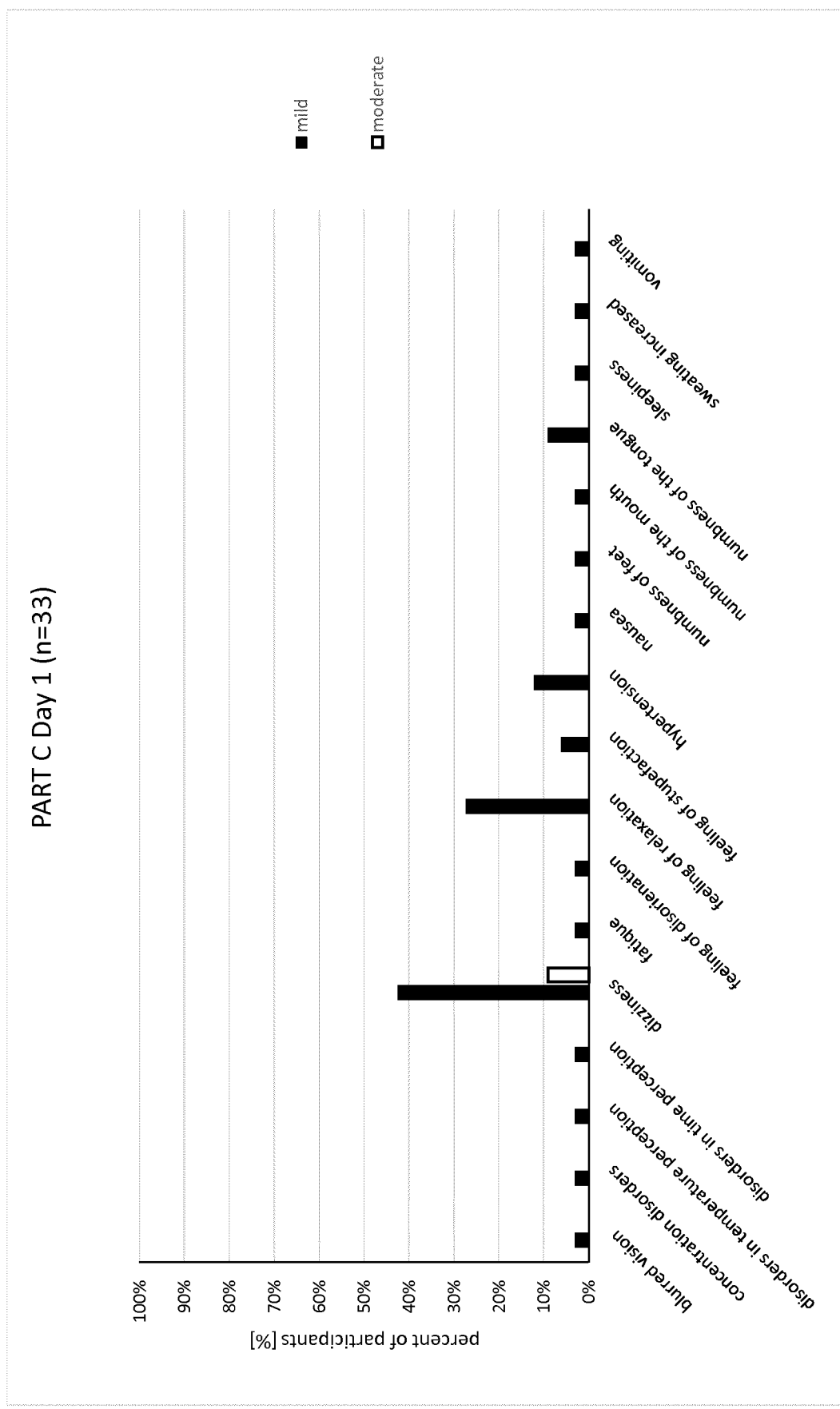
FIGS. 12A to 12D present adverse effect distribution after administration of dry powder composition of Example 2 on Day 1, Day 4, Day 8 and Day 11, respectively, in a cycle of administrations of sequences of single doses in Part C of the study.
Figure 12B:
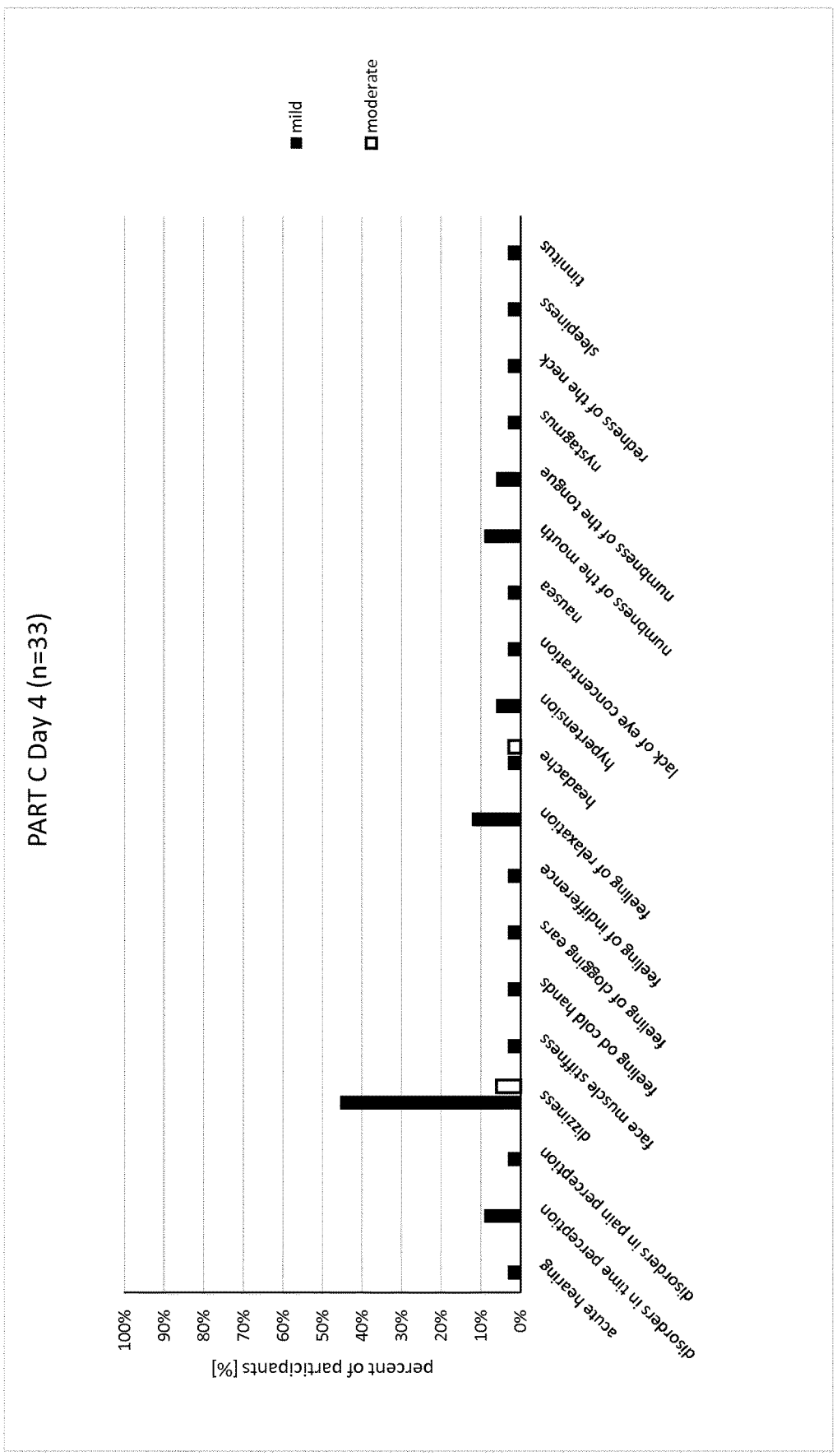
Figure 12C:
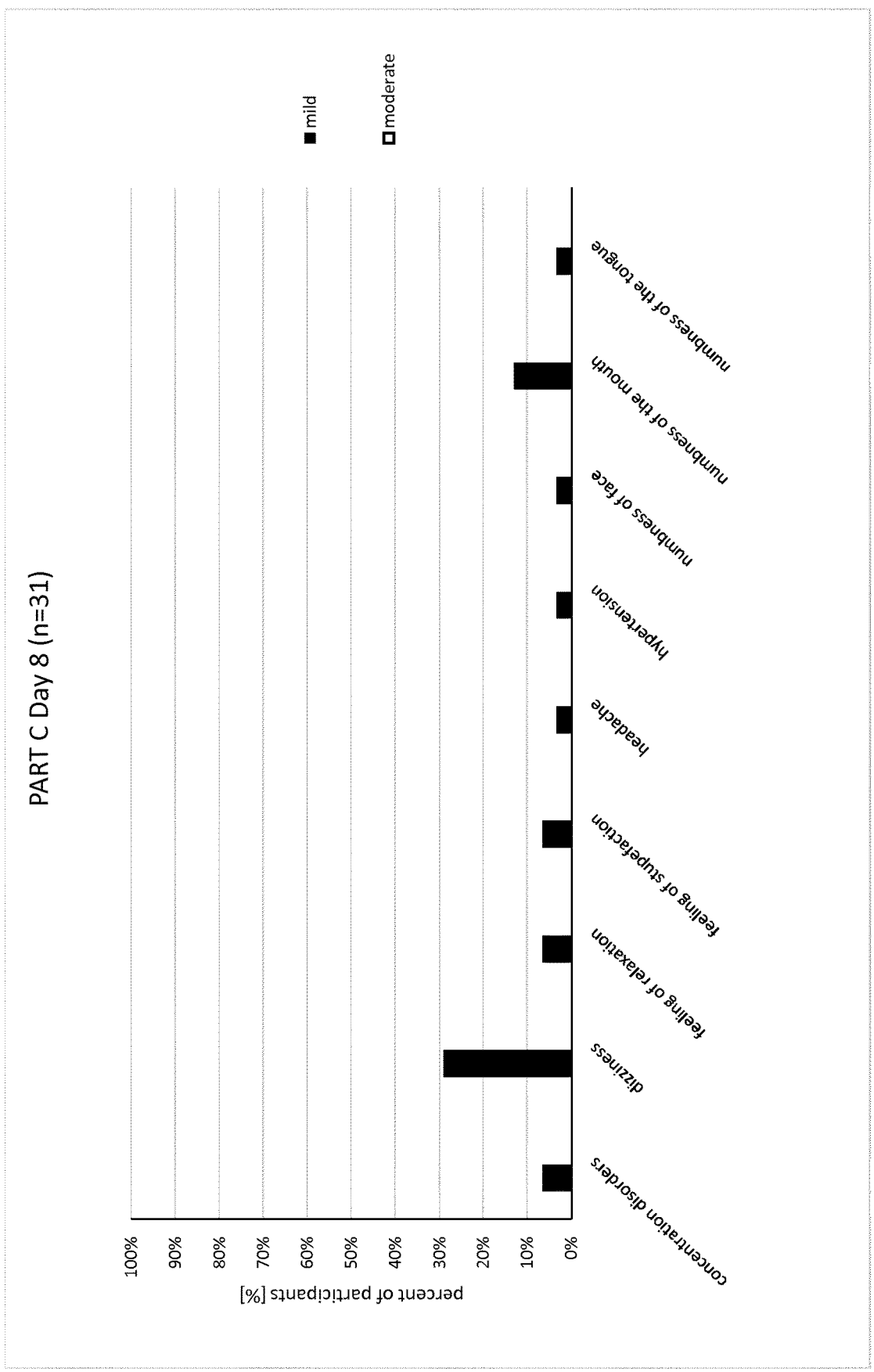
Figure 12D:
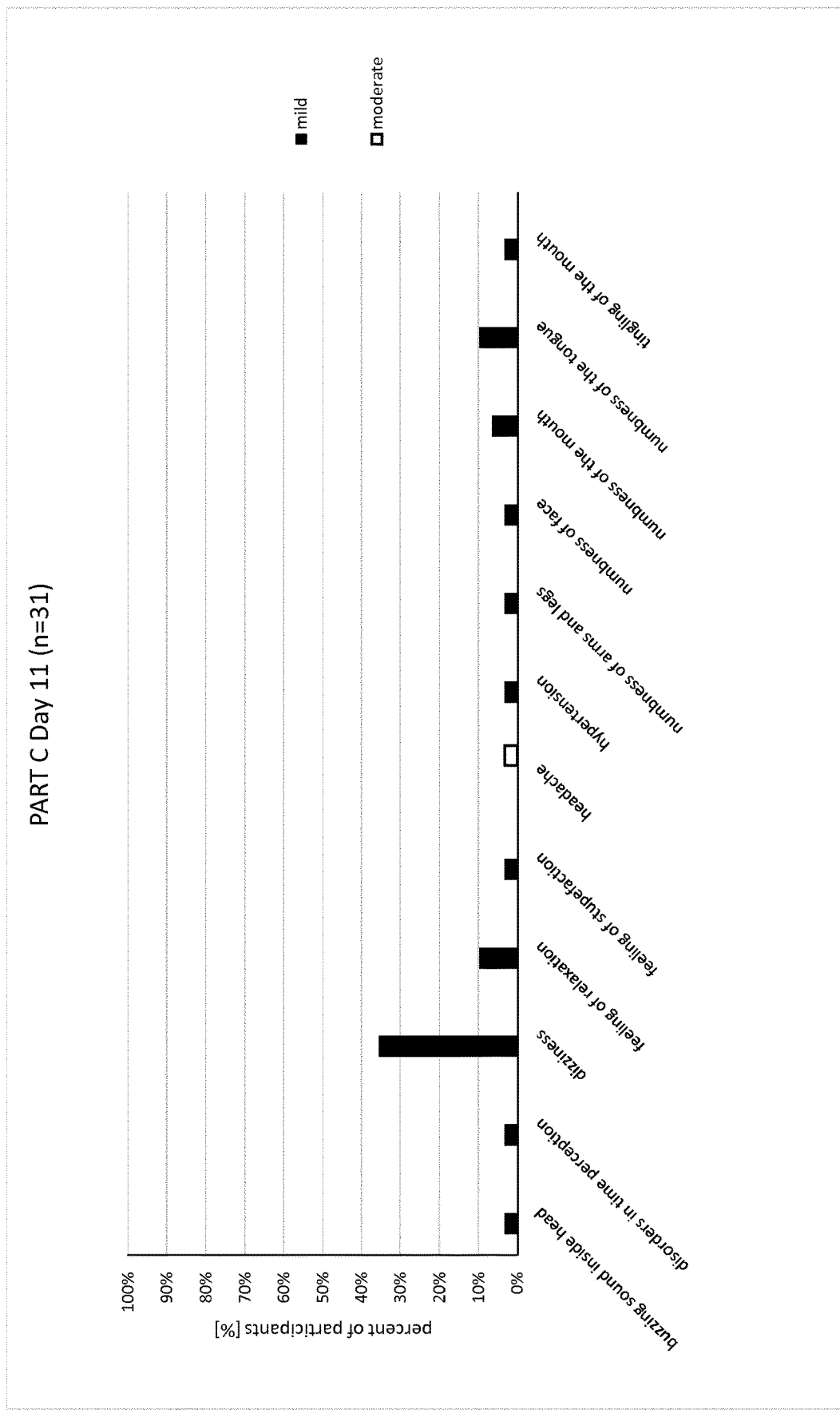

Both in Part A and Part B of the study the adverse effects were monitored and assessed by a psychiatrist. The summary of the adverse effects is presented in FIG. 10 (Part A) and FIG. 11 (Part B). As can be seen, no serious effects were observed, all adverse effects being assessed as mild, occasionally moderate. Psychomimetic effects were transient, lasting up to 30 minutes following administration. There were no discontinuations due to adverse effects or toxicity. In Part C of the study adverse effects were monitored and assessed by a psychiatrist after each sequence of administration, i.e. on Day 1, Day 4, Day 8 and Day 11. The summary of adverse effects for Part C is presented on FIGS. 12A to 12D for Day 1, Day 4, Day 8 and Day 11, respectively. Similarly as in Parts A and B, all adverse effects being assessed as mild, occasionally moderate. Psychomimetic effects were transient, lasting up to 30 minutes following administration. There were no discontinuations due to adverse effects or toxicity. Surprisingly, no aggravation of adverse effects was observed during a treatment cycle. On the contrary, reduction of adverse effects was observed in each subsequent treatment day in a cycle.

The above shows that pulmonary administration of esketamine, i.e. directly to the lungs is a promising way of treating depression, in particular major depressive disorder, bipolar disorder or TRD, by convenient self-administration by a patient. Plasma concentration profile is quite smooth, consistent with a target profile and safe for chronic administration.

The invention claimed is:

1. A method of ftreating depression in a subject comprising administration to the lungs of the subject via pulmonary route of an inhalable pharmaceutical composition comprising ketamine or its isomer or its pharmaceutically acceptable salt, wherein said treating is performed in a dosage regimen that comprises a 10 days to a 30 days cycle of multiple administrations by inhalation, wherein each administration of the multiple administrations is performed on a single day with an interval of 2 to 4 days between each administration, wherein each administration of the multiple administrations consists of a sequence of multiple single dose inhalations, and wherein each single dose inhalation in said sequence is separated by a break period lasting about 15 minutes.

2. The method according to claim 1, wherein the inhalable pharmaceutical composition is an inhalable dry powder composition.

3. The method according to claim 1 wherein pharmaceutically acceptable salt is hydrochloride.

4. The method according to claim 1 wherein ketamine is esketamine hydrochloride.

5. The method according to claim 1 wherein the inhalable pharmaceutical composition comprises one or more nominal unit doses of ketamine or its pharmaceutically acceptable salt, the ketamine or its pharmaceutically acceptable salt in the composition is in the form of micronized. ketamine, and said. micronized ketamine is present in the inhalable pharmaceutical composition in an amount of 2 mg to 100 mg calculated as a free base per nominal unit dose.

6. The method. according to claim 5, wherein the micronized. ketamine is micronized esketamine, and. said micronized esketamine is present in the inhalable pharmaceutical composition in an amount of 2 to 40 mg calculated as a free base per nominal unit dose.

7. The method according to claim 6, wherein the inhalable pharmaceutical composition comprises 4 mg of micronized esketamine calculated as a free base per nominal unit dose.

8. The method. according to claim. 2, wherein the inhalable dry powder composition further comprises one or more additives selected from the group consisting of a carbohydrate bulking agent in an amount of 30 to 95% by weight and a stabilizing agent in an amount of 0.2-3% by weight, with respect to the total weight of the composition.

9. The method. according to claim 2, wherein the inhalable dry powder composition comprises ketamine having median particle diameter d50 of 1-10 µm, d10 of 0.2-5 µm and d90 of 3-35 µm, as measured by laser diffraction technique.

10. The method according to claim 5, wherein the inhalable pharmaceutical composition. provides an emitted dose of at least 1.0 mg of ketamine calculated as a free base, corresponding to 1.2 mg of ketamine hydrochloride, wherein the emitted dose of ketamine is up to 97% of the amount of ketamine per nominal unit dose.

11. The method. according to claim 10, wherein the fraction of the emitted dose delivered to the lungs is from 40% to 85%.

12. The method according to claim 2, wherein the composition is incorporated in a blister with plurality of individual nominal unit doses premetered and individually sealed.

13. The method according to claim 2, wherein the composition is incorporated in a capsule with a single nominal unit dose.

14. The method according to claim 1, wherein the inhalable pharmaceutical composition is comprised in a multi-dose powder reservoir.

15. The method according to claim 1, wherein said cycle lasts 12 to 14 days and comprises 4 administrations separated by 3 to 4 day intervals, each of the 4 administrations consisting of a sequence of multiple single dose inhalations.

16. The method according claim 15, wherein the inhalable pharmaceutical composition comprises one or more nominal unit doses of ketamine or its pharmaceutically acceptable salt, the ketamine or its pharmaceutically acceptable salt in the composition. is in the form. of micronized ketamine, and said micronized ketamine is present in the inhalable pharmaceutical composition in an amount of 2 mg to 20 mg calculated as a free base per nominal unit dose.

17. The method according to claim 16, wherein the inhalable pharmaceutical composition provides an emitted dose inhalation of at least 1.0 mg of ketamine calculated as a free base, in the form of and. corresponding to 1.2 mg of ketamine hydrochloride, wherein the emitted dose of ketamine is up to 97% of the amount of ketamine per nominal unit dose.

18. A method of treatment of depression, by administration of an inhalable dry powder pharmaceutical composition comprising one or more nominal unit doses of micronized esketamine hydrochloride to the lungs via pulmonary route, wherein said treatment is performed in a dosage regimen that comprises a cycle of multiple sequences of administration by inhalation, said cycle lasting from 10 days to 30 days, wherein each of multiple sequences of administration is performed in a single day, with 2 to 4 day intervals between sequences, and each of said sequences consists of multiple single dose inhalations separated by a break period lasting from 5 to 15 minutes, wherein said micronized esketamine hydrochloride is present in the inhalable dry powder pharmaceutical composition in an amount of 2 mg to 20 mg calculated as a free base per nominal unit dose.

19. The method of claim 18, wherein each of said sequences of administration consists of three single dose inhalations.

20. The method of claim 17, wherein each administration of the multiple administrations consists of a sequence of three single dose inhalations.

* * * * *